United States Patent
Shimizu et al.

(10) Patent No.: US 10,696,711 B2
(45) Date of Patent: *Jun. 30, 2020

(54) ASYMMETRIC AUXILIARY GROUP

(71) Applicant: WAVE LIFE SCIENCES LTD., Singapore (SG)

(72) Inventors: Mamoru Shimizu, Arlington, MA (US); Takeshi Wada, Kashiwa (JP)

(73) Assignee: WAVE LIFE SCIENCES LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 16/182,302

(22) Filed: Nov. 6, 2018

(65) Prior Publication Data

US 2019/0177357 A1    Jun. 13, 2019

Related U.S. Application Data

(63) Continuation of application No. 15/294,602, filed on Oct. 14, 2016, now Pat. No. 10,167,309, which is a continuation of application No. 14/414,604, filed as application No. PCT/JP2013/004303 on Jul. 12, 2013, now Pat. No. 9,598,458.

(60) Provisional application No. 61/671,652, filed on Jul. 13, 2012.

(51) Int. Cl.
| | |
|---|---|
| *C07H 23/00* | (2006.01) |
| *C07B 53/00* | (2006.01) |
| *C07H 21/04* | (2006.01) |
| *C07H 1/00* | (2006.01) |
| *C07H 19/10* | (2006.01) |
| *C07H 19/207* | (2006.01) |
| *C07D 405/04* | (2006.01) |
| *C07D 473/18* | (2006.01) |
| *C07D 473/34* | (2006.01) |
| *C07H 19/11* | (2006.01) |
| *C07H 19/213* | (2006.01) |
| *C07D 207/08* | (2006.01) |
| *C07F 7/08* | (2006.01) |

(52) U.S. Cl.
CPC ............ *C07H 23/00* (2013.01); *C07B 53/00* (2013.01); *C07D 207/08* (2013.01); *C07D 405/04* (2013.01); *C07D 473/18* (2013.01); *C07D 473/34* (2013.01); *C07F 7/0812* (2013.01); *C07H 1/00* (2013.01); *C07H 19/10* (2013.01); *C07H 19/11* (2013.01); *C07H 19/207* (2013.01); *C07H 19/213* (2013.01); *C07H 21/04* (2013.01)

(58) Field of Classification Search
None
See application file for complete search history.

(56) References Cited

U.S. PATENT DOCUMENTS

| | | | |
|---|---|---|---|
| 10,144,933 B2 | 12/2018 | Gemba et al. | |
| 10,149,905 B2 | 12/2018 | Gemba et al. | |
| 10,160,969 B2 | 12/2018 | Meena et al. | |
| 10,167,309 B2 | 1/2019 | Shimizu et al. | |
| 10,280,192 B2 | 5/2019 | Verdine et al. | |
| 10,307,434 B2 | 6/2019 | Verdine et al. | |
| 10,322,173 B2 | 6/2019 | Gemba et al. | |
| 10,329,318 B2 | 6/2019 | Wada et al. | |
| 10,428,019 B2 | 10/2019 | Wada et al. | |
| 10,450,568 B2 | 10/2019 | Butler et al. | |
| 10,479,995 B2 | 11/2019 | Vargeese et al. | |
| 2018/0216107 A1 | 8/2018 | Frank-Kamenetsky et al. | |
| 2019/0077817 A1 | 3/2019 | Butler et al. | |
| 2019/0106696 A1 | 4/2019 | Meena et al. | |
| 2019/0127733 A1 | 5/2019 | Butler et al. | |
| 2019/0209604 A1 | 7/2019 | Zhang et al. | |
| 2019/0249173 A1 | 8/2019 | Vargeese et al. | |
| 2019/0264267 A1 | 8/2019 | Yang et al. | |
| 2019/0375774 A1 | 12/2019 | Butler et al. | |
| 2019/0390197 A1 | 12/2019 | Butler et al. | |

FOREIGN PATENT DOCUMENTS

| | | | |
|---|---|---|---|
| WO | WO-2005014609 A2 * | 2/2005 | ............ C07H 19/10 |
| WO | WO-2019/032607 A1 | 2/2019 | |
| WO | WO-2019/032612 A1 | 2/2019 | |
| WO | WO-2019/055951 A1 | 3/2019 | |
| WO | WO-2019/075357 A1 | 4/2019 | |
| WO | WO-2019/200185 A1 | 10/2019 | |
| WO | WO-2019/217784 A1 | 11/2019 | |

OTHER PUBLICATIONS

Tian, Mol. BioSyst., 2009, 5, 714-722. (Year: 2009).*

* cited by examiner

*Primary Examiner* — Layla D Berry
(74) *Attorney, Agent, or Firm* — Choate, Hall & Stewart LLP; Brenda Herschbach Jarrell; Xiaodong Li

(57) ABSTRACT

To provide a chiral reagent or a salt thereof.

The chiral reagent has following chemical formula (I). In the formula (I), $G^1$ and $G^2$ are independently a hydrogen atom, a nitro group (—$NO_2$), a halogen atom, a cyano group (—CN), a group of formula (II) or (III), or both $G^1$ and $G^2$ taken together to form a group of formula (IV).

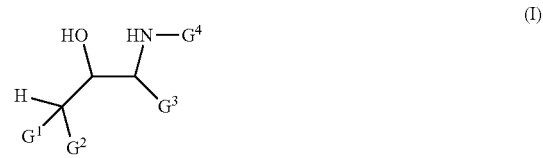

(I)

32 Claims, 2 Drawing Sheets

ASYMMETRIC AUXILIARY GROUP

FIELD OF THE INVENTION

The present invention is directed to a chiral reagent that is used to synthesize stereo-controlled phosphorus atom-modified oligonucleotide derivatives.

BACKGROUND OF THE INVENTION

JP 2005-89441 A discloses a method for producing a derivative of nucleotides called an oxazaphospholidine method. However, the isolate yield of the monomers is low and the method requires special capping agents that are not commercially available. Further obtained monomers are chemically unstable. Furthermore, the isolate yields of oligonucleotide derivatives are not high. It is thought that the low yield of oligonucleotide derivatives is caused by the degradation reactions under the de-protection steps.

WO2010/064146 pamphlet discloses a method for producing a derivative of nucleotides. The method disclosed therein requires special capping agents that are not commercially available. Furthermore, the isolate yields of oligonucleotide derivatives are not high. The low yield is thought to be caused by the degradation reactions under the de-protection steps. This tendency becomes strongly apparent when the length of oligonucleotide derivatives becomes long.

WO2012/039448 pamphlet discloses Asymmetric auxiliary group which is used to produce stereocontrolled phosphorus atom-modified oligonucleotide derivatives.

CITATION LIST

Patent Literature

[Patent Literature 1] JP 2005-89441 A
[Patent Literature 2] WO2010/064146 A
[Patent Literature 3] WO2012/039448 A

SUMMARY OF THE INVENTION

The first Aspect of the Invention relates to a chiral reagent or a salt thereof. The chiral reagent has following chemical formula (I).

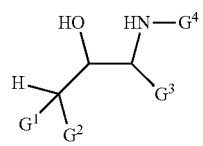

(I)

In the formula (I), $G^1$ and $G^2$ are independently a hydrogen atom, a nitro group (—$NO_2$), a halogen atom, a cyano group (—CN), a group of formula (II), (III) or (V), or both $G^1$ and $G^2$ taken together to form a group of formula (IV).

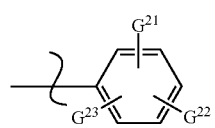

(II)

In the formula (II), $G^{21}$ to $G^{23}$ are independently a hydrogen atom, a nitro group, a halogen atom, a cyano group or $C_{1-3}$ alkyl group.

(III)

In the formula (III), $G^{31}$ to $G^{33}$ are independently $C_{1-4}$ alkyl group, $C_{6-14}$ aryl group $C_{1-4}$ alkoxy group, $C_{7-14}$ aralkyl group, $C_{1-4}$ alkyl $C_{6-14}$ aryl group, $C_{1-4}$ alkoxy $C_{6-14}$ aryl group, or $C_{6-14}$ aryl $C_{1-4}$ alkyl group.

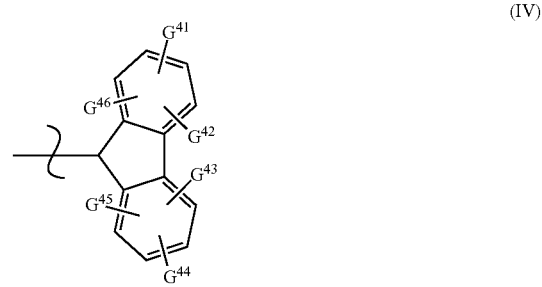

(IV)

In the formula (IV), $G^{41}$ to $G^{46}$ are independently a hydrogen atom, a nitro group, a halogen atom, a cyano group or $C_{1-3}$ alkyl group.

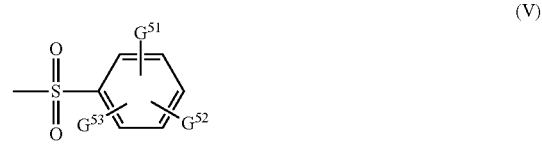

(V)

In the formula (V), $G^{51}$ to $G^{53}$ are independently a hydrogen atom, a nitro group, a halogen atom, a cyano group, $C_{1-3}$ alkyl group or $C_{1-3}$ alkyloxy group.

$G^3$ and $G^4$ are independently a hydrogen atom, $C_{1-3}$ alkyl group, $C_{6-14}$ aryl group, or both $G^3$ and $G^4$ taken together to form a heteroatom-containing ring that has 3 to 16 carbon atoms, together with the NH moiety in formula (I).

A preferred embodiment is that the chiral reagent has following chemical formula (I').

(I')

In the formula (I'), $G^1$ and $G^2$ are same as above. Namely, $G^1$ and $G^2$ are independently a hydrogen atom, a nitro group, a halogen atom, a cyano group, a group of formula (II) or (III), or both $G^1$ and $G^2$ taken together to form a group of formula (IV).

A preferred embodiment is that the chiral reagent has chemical formula (I') and each of $G^1$ and $G^2$ is a group of formula (II), wherein $G^{21}$ to $G^{23}$ are independently a hydrogen atom, a nitro group, a halogen atom, a cyano group or $C_{1-3}$ alkyl group.

A preferred embodiment is that the chiral reagent has chemical formula (I') and each of $G^1$ and $G^2$ is a group of formula (II) and each of $G^{21}$ to $G^{23}$ is a hydrogen atom A preferred embodiment is that the chiral reagent has chemical formula (I') and $G^1$ is a hydrogen atom, $G^2$ is a group of formula (II), and $G^{21}$ to $G^{23}$ are independently a hydrogen atom, a nitro group, a halogen atom, a cyano group or $C_{1-3}$ alkyl group.

A preferred embodiment is that the chiral reagent has chemical formula (I') and $G^1$ is a hydrogen atom, $G^2$ is a group of formula (II), each of $G^{21}$ and $G^{22}$ is a hydrogen atom and $G^{23}$ is a nitro group.

A preferred embodiment is that the chiral reagent has chemical formula (I') and $G^1$ is a hydrogen atom and $G^2$ is a group of formula (III), and $G^{31}$ to $G^{33}$ are independently $C_{1-4}$ alkyl group, $C_{6-14}$ aryl group, $C_{7-14}$ aralkyl group, $C_{1-4}$ alkyl $C_{6-14}$ aryl group, $C_{1-4}$ alkoxy $C_{6-14}$ aryl group, or $C_{6-14}$ aryl $C_{1-4}$ alkyl group.

A preferred embodiment is that the chiral reagent has chemical formula (I') and $G^1$ is a hydrogen atom and $G^2$ is a group of formula (III), and $G^{31}$ to $G^{33}$ are independently $C_{1-4}$ alkyl group, $C_6$ aryl group, $C_{7-10}$ aralkyl group, $C_{1-4}$ alkyl $C_6$ aryl group, $C_{1-4}$ alkoxy $C_6$ aryl group, or $C_6$ aryl $C_{1-4}$ alkyl group.

A preferred embodiment is that the chiral reagent has chemical formula (I') and $G^1$ is a hydrogen atom, $G^2$ is a group of formula (III), and $G^{31}$ to $G^{33}$ are independently $C_{1-4}$ alkyl group or $C_6$ aryl group. Examples of $C_{1-4}$ alkyl group are methyl group, ethyl group, n-propyl group, iso-propyl group, n-buthyl group and tert-buthyl group.

A preferred embodiment is that the chiral reagent has chemical formula (I') and $G^1$ is a hydrogen atom, $G^2$ is a group of formula (III), and $G^{31}$ to $G^{33}$ are independently $C_{1-4}$ alkyl group.

A preferred embodiment is that the chiral reagent has chemical formula (I') and $G^1$ is a hydrogen atom, $G^2$ is a group of formula (III), and $G^{31}$ and $G^{33}$ are $C_6$ aryl group and $G^{32}$ is $C_{1-4}$ alkyl group.

A preferred embodiment is that the chiral reagent has chemical formula (I') and $G^1$ and $G^2$ taken together to form a group of formula (IV), and $G^{41}$ to $G^{46}$ are independently a hydrogen atom, a nitro group, a halogen atom, a cyano group or $C_{1-4}$ alkyl group.

A preferred embodiment is that the chiral reagent has chemical formula (I') and $G^1$ and $G^2$ taken together to form a group of formula (IV), wherein each of $G^{41}$ to $G^{46}$ is a hydrogen atom.

A preferred embodiment is that the chiral reagent has chemical formula (I') and $G^1$ is a hydrogen atom and $G^2$ is a group of formula (V). Further each of $G^{51}$ to $G^{53}$ is independently a hydrogen atom, a nitro group, a methyl group, or a methoxy group. More preferred embodiment is that $G^1$ is a hydrogen atom and $G^2$ is a group of formula (V), wherein each of $G^{51}$ and $G^{53}$ is a hydrogen atom and $G^{53}$ is a 4-methyl group.

A preferred embodiment is that the chiral reagent is selected from one of III-a, III-b, V-a, VII-a, VII-b, IX-a, IX-b, XI-a, XIII-a and XIII-b:

(S)-2-(Methyldiphenylsilyl)-1-((S)-pyrrolidin-2-yl)ethanol (III-a)
(R)-2-(Methyldiphenylsilyl)-1-((R)-1-pyrrolidin-2-yl)ethanol (III-b)
(S)-2-(Trimethylsilyl)-1-((S)-1-pyrrolidin-2-yl)ethanol (V-a)
(R)-2,2-Diphenyl-1-((S)-pyrrolidin-2-yl)ethanol (VII-a)
(S)-2,2-Diphenyl-1-((R)-pyrrolidin-2-yl)ethanol (VII-b)
(R)-2-(4-Nitrophenyl)-1-((S)-pyrrolidin-2-yl)ethanol (IX-a)
(S)-2-(4-Nitrophenyl)-1-((R)-pyrrolidin-2-yl)ethanol (IX-b)
(R)-(9H-Fluororen-9-yl)((S)-pyrrolidin-2-yl)methanol (XI-a)
(S)-2-Tosyl-1-((S)-1-tritylpyrrolidin-2-yl)ethanol (XIII-a)
(R)-2-Tosyl-1-((R)-1-tritylpyrrolidin-2-yl)ethanol (XIII-b)

The second aspect of the invention relates to a nucleoside 3'-phosphoramidite derivative which is represented by formula (Va) or (Vb).

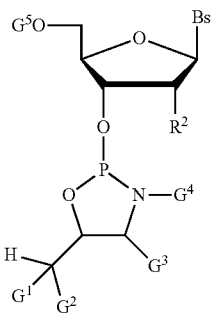

(Va)

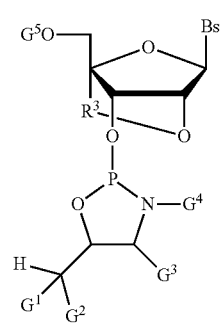

(Vb)

In the formula (Va) and (Vb), $G^1$ to $G^4$ are same as above, $G^5$ is a protective group of the hydroxyl group, and Bs is a group selected from the groups represented by following formula (VI) to (XI) or derivatives thereof.

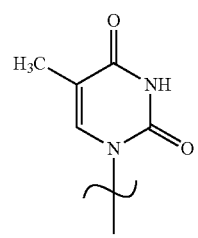

(VI)

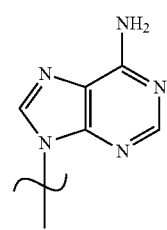

(VII)

-continued

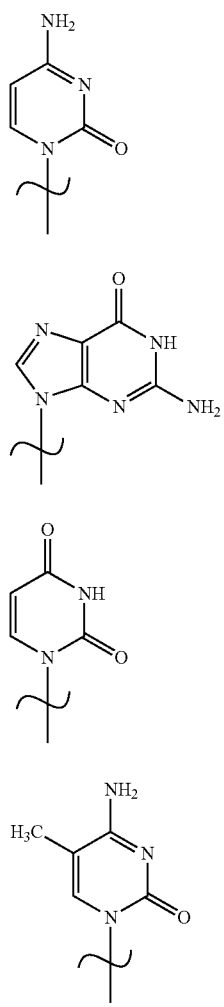

(VIII)

(IX)

(X)

(XI)

Examples of Bs are an adenine, a thymine, a cytosine, a guanine, an uracil, a 5-methylcytosine or derivative thereof.

$R^2$ is hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^b$, wherein R$^b$ is a blocking moiety.

$Y^1$ is O, NR$^d$, S, or Se.

$R^d$ is independently hydrogen, alkyl, alkenyl, alkynyl, aryl, acyl, substituted silyl, carbamate, —P(O)(R$^c$)$_2$, or —HP(O)(R$^c$).

$R^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^+$, Li$^+$, or K$^+$.

$Y^2$ is O, NR$^d$, or S.

$R^3$ is a group represented by —CH$_2$—, —(CH$_2$)$_2$—, —CH$_2$NH—, or —CH$_2$N(CH$_3$)—.

Examples of G$^5$ are trityl, 4-monomethoxytrityl, 4,4'-dimethoxytrityl, 4,4',4''-trimethoxytrityl, 9-phenylxanthin-9-yl (Pixyl) and 9-(p-methoxyphenyl)xanthin-9-yl (MOX).

A preferred embodiment of the second aspect is that the nucleoside 3'-phosphoramidite derivative is represented by formula (Va') or (Vb').

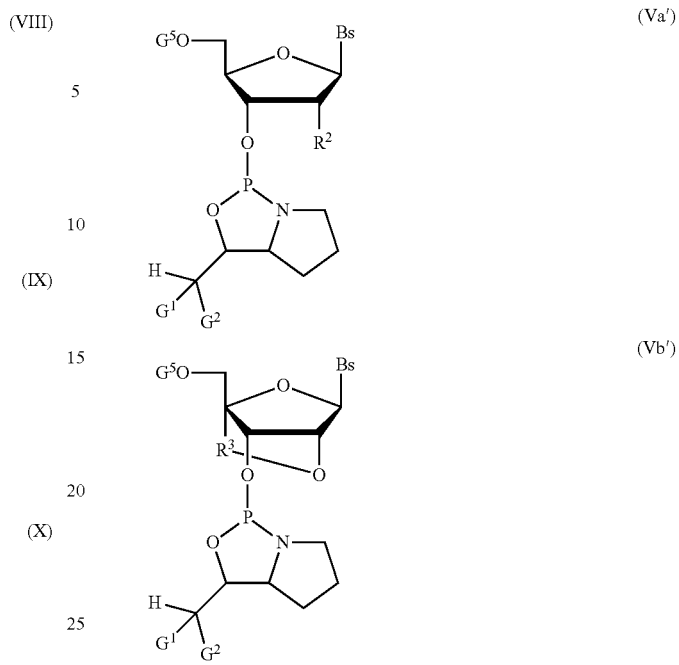

(Va')

(Vb')

In the formula (Va') and (Vb'), G$^1$, G$^2$, G$^5$, Bs, R$^2$, and R$^3$ are same as above.

The third aspect of the invention relates to a method for synthesis of a stereocontrolled phosphorus atom-modified oligonucleotide derivative.

First step is a step of reacting a molecule comprising an achiral H-phosphonate moiety, the first activating reagent and a chiral reagent or a salt thereof to form a monomer. The chiral reagent has chemical formula (I) or (I') and the monomer may be represented by formula (Va), (Vb), (Va'), or (Vb'). The monomer reacts with the second activating reagent and a nucleoside to form a condensed intermediate. Next step is a step of converting the condensed intermediate to the nucleic acid comprising a chiral X-phosphonate moiety.

Based on the present method, it is possible to use stable and commercially available materials as starting materials. It is possible to produce stereocontrolled phosphorus atom-modified oligonucleotide derivatives using an achiral starting material.

As shown in a working example, the method of the present invention does not cause degradations under deprotection steps. Further the method does not require special capping agents to produce phosphorus atom-modified oligonucleotide derivatives.

The fourth aspect of the invention relates to a method for synthesis of stereocontrolled phosphorus atom-modified oligonucleotide derivatives using a chiral monomer.

The first step is reacting a nucleoside 3'-phosphoramidite derivative which is represented by formula (Va), (Vb), (Va'), or (Vb') with the second activating reagent and a nucleoside to form a condensed intermediate. The second step is converting the condensed intermediate to the nucleic acid comprising a chiral X-phosphonate moiety.

INCORPORATION BY REFERENCE

All publications and patent applications disclosed herein in this specification are herein incorporated by reference in their entirety to the same extent as if each individual publication or patent application was specifically and individually indicated to be incorporated by reference.

BEST MODE FOR CARRYING OUT THE INVENTION

Figure 1:
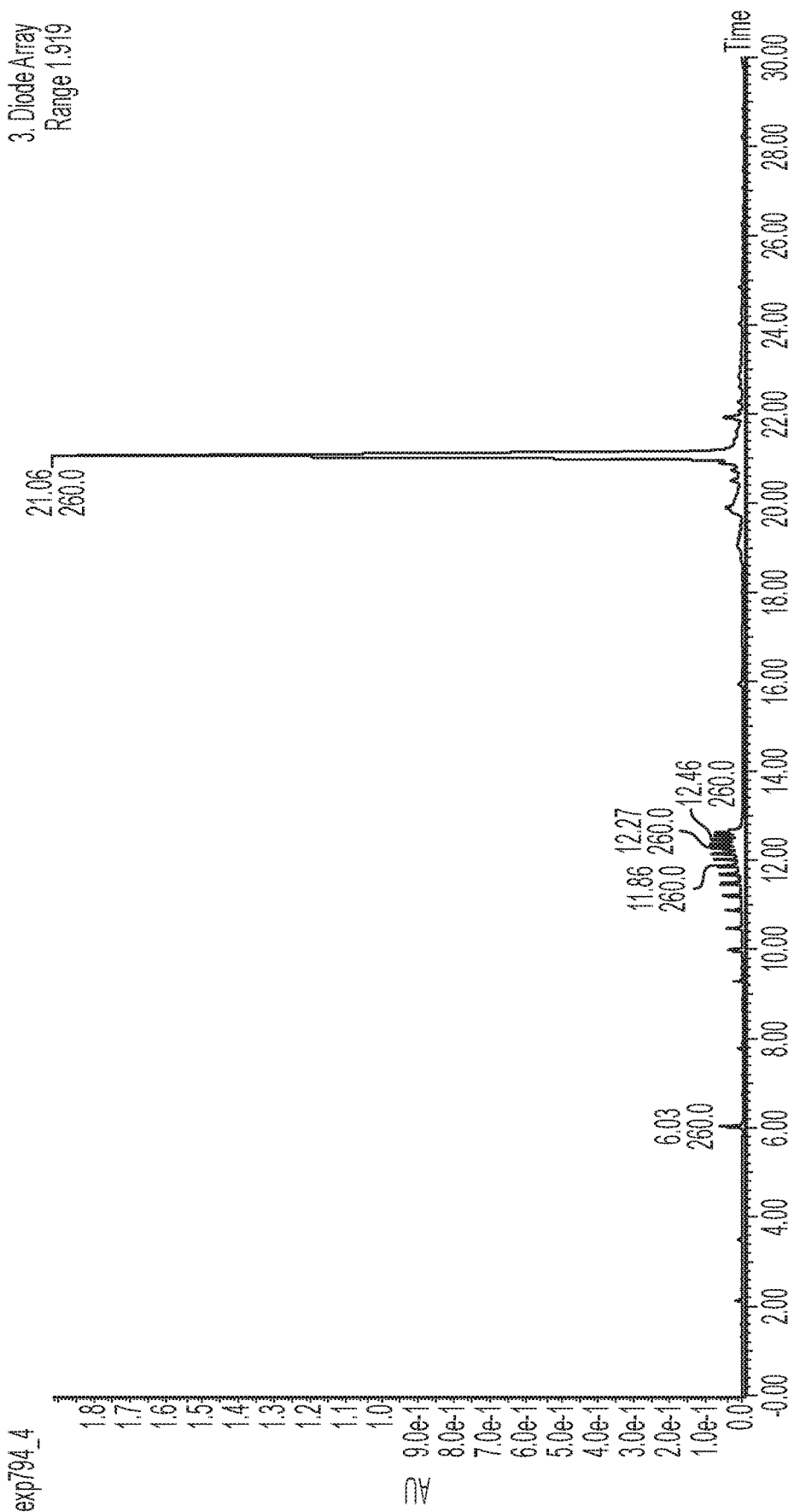
FIG. 1 is UPLC profile in producing oligonucleotide derivative using the monomer of 4b.

The term "nucleic acid" encompasses poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorus-atom bridges. The term encompasses nucleic acids containing any combinations of nucleobases, modified nucleobases, sugars, modified sugars, phosphate bridges or modified phosphorus atom bridges. Examples include, and are not limited to, nucleic acids containing ribose moieties, the nucleic acids containing deoxyribose moieties, nucleic acids containing both ribose and deoxyribose moieties, nucleic acids containing ribose and modified ribose moieties. The prefix poly- refers to a nucleic acid containing about 1 to about 10,000 nucleotide monomer units and wherein the prefix oligo- refers to a nucleic acid containing about 1 to about 200 nucleotide monomer units.

The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), 5-methylcytosine, and thymine (T).

The term "modified nucleobase" refers to a moiety that can replace a nucleobase. The modified nucleobase mimics the spatial arrangement, electronic properties, or some other physicochemical property of the nucleobase and retains the property of hydrogen-bonding that binds one nucleic acid strand to another in a sequence specific manner. A modified nucleobase can pair with all of the five naturally occurring bases (uracil, thymine, adenine, cytosine, or guanine) without substantially affecting the melting behaviour, recognition by intracellular enzymes or activity of the oligonucleotide duplex.

The term "nucleoside" refers to a moiety wherein a nucleobase or a modified nucleobase is covalently bound to a sugar or modified sugar.

The term "sugar" refers to a monosaccharide in closed and/or open form. Sugars include, but are not limited to, ribose, deoxyribose, pentofuranose, pentopyranose, and hexopyranose moieties.

The term "modified sugar" refers to a moiety that can replace a sugar. The modified sugar mimics the spatial arrangement, electronic properties, or some other physicochemical property of a sugar.

The term "nucleotide" refers to a moiety wherein a nucleobase or a modified nucleobase is covalently linked to a sugar or modified sugar, and the sugar or modified sugar is covalently linked to a phosphate group or a modified phosphorus-atom moiety.

The term "chiral reagent" refers to a compound that is chiral or enantiopure and can be used for asymmetric induction in nucleic acid synthesis.

The term "chiral ligand" or "chiral auxiliary" refers to a moiety that is chiral or enantiopure and controls the stereochemical outcome of a reaction.

In a condensation reaction, the term "activating reagent" refers to a reagent that activates a less reactive site and renders it more susceptible to attack by a nucleophile.

The term "blocking moiety" refers to a group that transiently masks the reactivity of a functional group. The functional group can be subsequently unmasked by removal of the blocking moiety.

The terms "boronating agents", "sulfur electrophiles", "selenium electrophiles" refer to compounds that are useful in the modifying step used to introduce $BH_3$, S, and Se groups, respectively, for modification at the phosphorus atom.

The term "moiety" refers to a specific segment or functional group of a molecule. Chemical moieties are often recognized chemical entities embedded in or appended to a molecule.

The term "solid support" refers to any support which enables synthetic mass production of nucleic acids and can be reutilized at need. As used herein, the term refers to a polymer that is insoluble in the media employed in the reaction steps performed to synthesize nucleic acids, and is derivatized to comprise reactive groups.

The term "linking moiety" refers to any moiety optionally positioned between the terminal nucleoside and the solid support or between the terminal nucleoside and another nucleoside, nucleotide, or nucleic acid.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

An "alkyl" group refers to an aliphatic hydrocarbon group. The alkyl moiety may be a saturated alkyl group (which means that it does not contain any units of unsaturation, e.g. carbon-carbon double bonds or carbon-carbon triple bonds) or the alkyl moiety may be an unsaturated alkyl group (which means that it contains at least one unit of unsaturation). The alkyl moiety, whether saturated or unsaturated, may be branched, straight chain, or include a cyclic portion. The point of attachment of an alkyl is at a carbon atom that is not part of a ring.

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). Alkyl includes both branched and straight chain alkyl groups. The alkyl group of the compounds described herein may be designated as "$C_1$-$C_6$ alkyl" or similar designations. By way of example only, "$C_1$-$C_6$ alkyl" indicates that there are one, two, three, four, five, or six carbon atoms in the alkyl chain, i.e., the alkyl chain is selected from the group consisting of methyl, ethyl, propyl, iso-propyl, n-butyl, iso-butyl, sec-butyl, and tert-butyl. Typical alkyl groups include, but are in no way limited to, methyl, ethyl, propyl, isopropyl, butyl, isobutyl, tertiary butyl, pentyl, hexyl, allyl, cyclopropylmethyl, cyclobutylmethyl, cyclopentylmethyl, cyclohexylmethyl, and the like. In one aspect, an alkyl is a $C_1$-$C_6$ alkyl.

$C_{1-3}$ alkyl group means straight or branched alkyl group that has 1 to 3 carbon atoms. Examples of $C_{1-3}$ alkyl group are methyl, ethyl, propyl and isopropyl. $C_{1-4}$ alkyl group means straight or branched alkyl group that has 1 to 4 carbon atoms. Examples of $C_{1-4}$ alkyl group are methyl, ethyl, propyl, isopropyl, butyl, isobutyl, and tert-butyl.

As used herein, the term "aryl" refers to an aromatic ring wherein each of the atoms forming the ring is a carbon atom. Aryl rings are formed by five, six, seven, eight, nine, or more than nine carbon atoms. Aryl groups are a substituted or unsubstituted. In one aspect, an aryl is a phenyl or a naphthalenyl. Depending on the structure, an aryl group can be a monoradical or a diradical (i.e., an arylene group). In one aspect, an aryl is a $C_6$-$C_{10}$ aryl.

$C_{6-14}$ aryl group means aryl group that has 6 to 14 carbon atoms. The examples of $C_{6-14}$ aryl group are phenyl, biphenyl, naphthyl, anthracyl, indanyl, phthalimidyl, naph-thimidyl, phenanthridinyl, and tetrahydronaphthyl.

The term "aralkyl" refers to an alkyl group substituted with an aryl group. Suitable aralkyl groups include benzyl, picolyl, and the like, all of which may be optionally substituted.

An "acyl moiety" refers to an alkyl(C=O), aryl(C=O), or aralkyl(C=O) group. An acyl moiety can have an intervening moiety (Y) that is oxy, amino, thio, or seleno between the carbonyl and the hydrocarbon group. For example, an acyl group can be alkyl-Y—(C=O), aryl-Y—(C=O) or aralkyl-Y—(C=O).

"Alkenyl" groups are straight chain, branch chain, and cyclic hydrocarbon groups containing at least one carbon-carbon double bond. Alkenyl groups can be substituted.

"Alkynyl" groups are straight chain, branch chain, and cyclic hydrocarbon groups containing at least one carbon-carbon triple bond. Alkynyl groups can be substituted.

An "alkoxy" group refers to an alklyl group linked to oxygen i.e. (alkyl)-O— group, where alkyl is as defined herein. Examples include methoxy (—OCH$_3$) or ethoxy (—OCH$_2$CH$_3$) groups.

An "alkenyloxy" group refers to an alkenyl group linked to oxygen i.e. (alkenyl)-O— group, where alkenyl is as defined herein.

An "alkynyloxy" group refers to an alkynyl group linked to oxygen i.e. (alkynyl)-O— group, where alkynyl is as defined herein.

An "aryloxy" group refers to an aryl group linked to oxygen i.e. (aryl)-O— group, where the aryl is as defined herein. An example includes phenoxy (—CO$_6$H$_5$) group.

The term "alkylseleno" refers to an alkyl group having a substituted seleno group attached thereto i.e. (alkyl)-Se— group, wherein alkyl is defined herein.

The term "alkenylseleno" refers to an alkenyl group having a substituted seleno group attached thereto i.e. (alkenyl)-Se— group, wherein alkenyl is defined herein.

The term "alkynylseleno" refers to an alkynyl group having a substituted seleno group attached thereto i.e. (alkynyl)-Se— group, wherein alkenyl is defined herein.

The term "alkylthio" refers to an alkyl group attached to a bridging sulfur atom i.e. (alkyl)-S— group, wherein alkyl is defined herein. For example, an alkylthio is a methylthio and the like.

The term "alkenylthio" refers to an alkenyl group attached to a bridging sulfur atom i.e. (alkenyl)-S— group, wherein alkenyl is defined herein.

The term "alkynylthio" refers to an alkynyl group attached to a bridging sulfur atom i.e. (alkynyl)-S— group, wherein alkenyl is defined herein.

The term "alkylamino" refers to an amino group substituted with at least one alkyl group i.e. —NH(alkyl) or —N(alkyl)$_2$, wherein alkyl is defined herein.

The term "alkenylamino" refers to an amino group substituted with at least one alkenyl group i.e. —NH(alkenyl) or —N(alkenyl)$_2$, wherein alkenyl is defined herein.

The term "alkynylamino" refers to an amino group substituted with at least one alkynyl group i.e. —NH(alkynyl) or —N(alkynyl)$_2$, wherein alkynyl is defined herein.

The term "halogen" is intended to include fluorine, chlorine, bromine and iodine.

A "fluorescent group" refers to a molecule that, when excited with light having a selected wavelength, emits light of a different wavelength. Fluorescent groups include, but are not limited to, indole groups, fluorescein, tetramethylrhodamine, Texas Red, BODIPY, 5-[(2-aminoethyl)amino] napthalene-1-sulfonic acid (EDANS), coumarin and Lucifer yellow.

An "ammonium ion" is a positively charged polyatomic cation of the chemical formula $NH_4^+$.

An "alkylammonium ion" is an ammonium ion that has at least one of its hydrogen atoms replaced by an alkyl group, wherein alkyl is defined herein. Examples include triethylammonium ion, N,N-diisopropylethylammonium ion.

An "iminium ion" has the general structure $R_2C=NR_2^+$. The R groups refer to alkyl, alkenyl, alkynyl, aryl groups as defined herein. A "heteroaromatic iminium ion" refers to an imminium ion where the nitrogen and its attached R groups form a heteroaromatic ring. A "heterocyclic iminium ion" refers to an imminium ion where the nitrogen and its attached R groups form a heterocyclic ring.

The terms "amino" or "amine" refers to a —N($R^h$)$_2$ radical group, where each $R^h$ is independently hydrogen, alkyl, fluoroalkyl, carbocyclyl, carbocyclyl alkyl, aryl, aralkyl, heterocyclyl, heterocyclylalkyl, heteroaryl or heteroarylalkyl, unless stated otherwise specifically in the specification. When a —N($R^h$)$_2$ group has two $R^h$ other than hydrogen they can be combined with the nitrogen atom to form a 4-, 5-, 6-, or 7-membered ring. For example, —N($R^h$)$_2$ is meant to include, but not be limited to, 1-pyrrolidinyl and 4-morpholinyl. Any one or more of the hydrogen, alkyl, fluoroalkyl, carbocyclyl, carbocyclylalkyl, aryl, aralkyl, heterocyclyl, heterocyclylalkyl, heteroaryl or heteroarylalkyl are optionally substituted by one or more substituents which independently are alkyl, heteroalkyl, alkenyl, alkynyl, cycloalkyl, heterocycloalkyl, aryl, aryl alkyl, heteroaryl, heteroaryl alkyl, hydroxy, halo, cyano, trifluoromethyl, trifluoromethoxy, nitro, trimethylsilyl, —OC(O)

$R^i$, —$SR^i$, —$OC(O)R^i$, —$N(R^i)_2$, —$C(O)R^i$, —$C(O)OR^i$, —$OC(O)N(R^i)_2$, —$C(O)N(R^i)_2$, —$N(R^i)C(O)OR$, —$N(R^i)C(O)R^i$, —$N(R^i)C(O)N(R^i)_2$, $N(R^i)C(NR^i)N(R^i)_2$, —$N(R^i)S(O)_tR^i$ (where t is 1 or 2), —$S(O)$, or —$S(O)_tN(R^i)_2$ (where t is 1 or 2), where each $R^i$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Carbamate" as used herein, refers to a moiety attached to an amino group which has the formula —C(O)OR where R is alkyl, fluoroalkyl, carbocyclyl, carbocyclylalkyl, aryl, aralkyl, heterocyclyl, heterocyclylalkyl, heteroaryl or heteroarylalkyl. Examples include but are not limited to Boc (tert-butyl-OC(O)—), CBz (benzyl-OC(O)—), Teoc (Me$_3$SiCH$_2$CH$_2$OC(O)—), alloc (allyl-OC(O)—), or Fmoc (9-fluorenylmethyl-OC(O)—) group.

"Substituted silyl" as used herein, refers to a moiety which has the formula R$_3$Si—. Examples include, but are not limited to, TBDMS (tert-butyldimethylsilyl), TBDPS (tert-butyldiphenylsilyl) or TMS (trimethylsilyl) group.

The term "thiol" refers to —SH groups, and include substituted thiol groups i.e. —$SR^J$ groups, wherein $R^J$ are each independently a substituted or unsubstituted alkyl, cycloalkyl, alkenyl, alkynyl, aryl aralkyl, heterocyclyl or heterocyclylalkyl group as defined herein.

The first aspect of the invention relates to a chiral reagent or a salt thereof. The chiral reagent has following chemical formula (I). The term "chiral reagent" is a chemical composition which is used to produce stereocontrolled phosphorus atom-modified nucleotide or oligonucleotide derivatives. The chiral reagent reacts with a nucleotide to form a chiral intermediate.

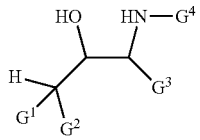

(I)

In the formula (I), $G^1$ and $G^2$ are independently a hydrogen atom, a nitro group, a halogen atom, a cyano group (—CN), a group of formula (II), (III) or (V), or both $G^1$ and $G^2$ taken together to form a group of formula (IV).

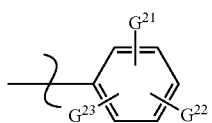

(II)

In the formula (II), $G^{21}$ to $G^{23}$ are independently a hydrogen atom, a nitro group, a halogen atom, a cyano group or $C_{1-3}$ alkyl group. Preferred examples of $G^{21}$ to $G^{23}$ are a hydrogen atom.

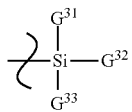

(III)

In the formula (III), $G^{31}$ to $G^{33}$ are independently $C_{1-4}$ alkyl group, $C_{6-14}$ aryl group $C_{1-4}$ alkoxy group, $C_{7-14}$ aralkyl group, $C_{1-4}$ alkyl $C_{6-14}$ aryl group, $C_{1-4}$ alkoxy $C_{6-14}$ aryl group, or $C_{6-14}$ aryl $C_{1-4}$ alkyl group. Examples of $C_{1-4}$ alkyl $C_{6-14}$ aryl group are methylphenyl group, and ethylphenyl group. Examples of $C_{1-4}$ alkoxy $C_{6-14}$ aryl group are a methoxyphenyl group and an ethoxyphenyl group. Examples of $C_{6-14}$ aryl $C_{1-4}$ alkyl groups are a benzyl group and a phenylethyl group. Preferred examples of $G^{31}$ to $G^{33}$ are independently a methyl group and a phenyl group.

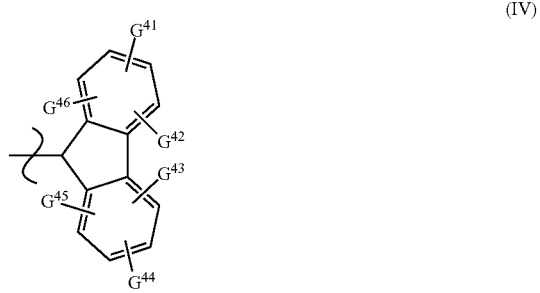

(IV)

In the formula (IV), $G^{41}$ to $G^{46}$ are independently a hydrogen atom, a nitro group, a halogen atom, a cyano group or $C_{1-3}$ alkyl group. Preferred examples of $G^{41}$ to $G^{46}$ are a hydrogen atom.

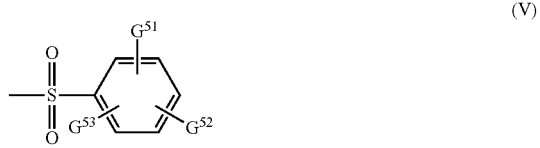

(V)

In the formula (V), $G^{51}$ to $G^{53}$ are independently a hydrogen atom, a nitro group, a halogen atom, a cyano group, $C_{1-3}$ alkyl group or $C_{1-3}$ alkyloxy group.

$G^3$ and $G^4$ are independently a hydrogen atom, $C_{1-3}$ alkyl group, $C_{6-14}$ aryl group, or both $G^3$ and $G^4$ taken together to form a heteroatom-containing ring that has 3 to 16 carbon atoms. Preferred examples of $G^3$ and $G^4$ are that taken together to form a heteroatom-containing ring that has 3 to 16 carbon atoms with NH moiety in the formula (I).

A preferred embodiment is that the chiral reagent has following chemical formula (I').

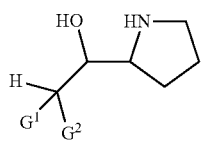

(I')

In the formula (I'), $G^1$ and $G^2$ are same as above and $G^1$ and $G^2$ are independently a hydrogen atom, a nitro group, a halogen atom, a cyano group, a group of formula (II) or (III), or both $G^1$ and $G^2$ taken together to form a group of formula (IV).

A preferred embodiment is that the chiral reagent has chemical formula (I') and each of $G^1$ and $G^2$ is a group of formula (II), wherein $G^{21}$ to $G^{23}$ are independently a hydrogen atom, a nitro group, a halogen atom, a cyano group or $C_{1-3}$ alkyl group.

A preferred embodiment is that the chiral reagent has chemical formula (I') and each of $G^1$ and $G^2$ is a group of formula (II) and each of $G^{21}$ to $G^{23}$ is a hydrogen atom.

A preferred embodiment is that the chiral reagent has chemical formula (I') and $G^1$ is a hydrogen atom, $G^2$ is a group of formula (II), and $G^{21}$ to $G^{23}$ are independently a hydrogen atom, a nitro group, a halogen atom, a cyano group or $C_{1-3}$ alkyl group.

A preferred embodiment is that the chiral reagent has chemical formula (I') and $G^1$ is a hydrogen atom, $G^2$ is a group of formula (II), each of $G^{21}$ and $G^{22}$ is a hydrogen atom and $G^{23}$ is a nitro group ($-NO_2$).

A preferred embodiment is that the chiral reagent has chemical formula (I') and $G^1$ is a hydrogen atom and $G^2$ is a group of formula (III), and $G^{31}$ to $G^{33}$ are independently $C_{1-4}$ alkyl group, $C_{6-14}$ aryl group, $C_{7-14}$ aralkyl group, $C_{1-4}$ alkyl $C_{6-14}$ aryl group, $C_{1-4}$ alkoxy $C_{6-14}$ aryl group, or $C_{6-14}$ aryl $C_{1-4}$ alkyl group.

A preferred embodiment is that the chiral reagent has chemical formula (I') and $G^1$ is a hydrogen atom and $G^2$ is a group of formula (III), and $G^{31}$ to $G^{33}$ are independently $C_{1-4}$ alkyl group, $C_6$ aryl group, $C_{7-10}$ aralkyl group, $C_{1-4}$ alkyl $C_6$ aryl group, $C_{1-4}$ alkoxy $C_6$ aryl group, or $C_6$ aryl $C_{1-4}$ alkyl group.

A preferred embodiment is that the chiral reagent has chemical formula (I') and $G^1$ is a hydrogen atom, $G^2$ is a group of formula (III), and $G^{31}$ to $G^{33}$ are independently $C_{1-4}$ alkyl group or $C_6$ aryl group (a phenyl group). Examples of $C_{1-4}$ alkyl group are methyl group, ethyl group, n-propyl group, iso-propyl group, n-butyl group and tert-butyl group.

A preferred embodiment is that the chiral reagent has chemical formula (I') and $G^1$ is a hydrogen atom, $G^2$ is a group of formula (III), and $G^{31}$ to $G^{33}$ are independently $C_{1-4}$ alkyl group.

A preferred embodiment is that the chiral reagent has chemical formula (I') and $G^1$ is a hydrogen atom, $G^2$ is a group of formula (III), and $G^{31}$ and $G^{33}$ are $C_6$ aryl group (a phenyl group) and $G^{32}$ is $C_{1-2}$ alkyl group.

A preferred embodiment is that the chiral reagent has chemical formula (I') and $G^1$ and $G^2$ taken together to form a group of formula (IV), and $G^{41}$ to $G^{46}$ are independently a hydrogen atom, a nitro group, a halogen atom, a cyano group or $C_{1-3}$ alkyl group.

A preferred embodiment is that the chiral reagent has chemical formula (I') and $G^1$ and $G^2$ taken together to form a group of formula (IV), wherein each of $G^{41}$ to $G^{46}$ is a hydrogen atom.

A preferred embodiment is that the chiral reagent has chemical formula (I') and $G^1$ is a hydrogen atom and $G^2$ is a group of formula (V). Further each of $G^{51}$ to $G^{53}$ is independently a hydrogen atom, a nitro group, a methyl group, or a methoxy group. More preferred embodiment is that $G^1$ is a hydrogen atom and $G^2$ is a group of formula (V), wherein each of $G^{51}$ and $G^{53}$ is a hydrogen atom and $G^{53}$ is a 4-methyl group.

A preferred embodiment is that the chiral reagent is selected from one of III-a, III-b, V-a, VII-a, VII-b, IX-a, IX-b, XI-a, XIII-a and XIII-b:

(S)-2-(Methyldiphenylsilyl)-1-((S)-pyrrolidin-2-yl)ethanol (III-a)

(R)-2-(Methyldiphenylsilyl)-1-((R)-1-pyrrolidin-2-yl)ethanol (III-b)

(S)-2-(Trimethylsilyl)-1-((S)-1-pyrrolidin-2-yl)ethanol (V-a)

(R)-2,2-Diphenyl-1-((S)-pyrrolidin-2-yl)ethanol (VII-a)
(S)-2,2-Diphenyl-1-((R)-pyrrolidin-2-yl)ethanol (VII-b)
(R)-2-(4-Nitrophenyl)-1-((S)-pyrrolidin-2-yl)ethanol (IX-a)
(S)-2-(4-Nitrophenyl)-1-((R)-pyrrolidin-2-yl)ethanol (IX-b)
(R)-(9H-Fluororen-9-yl)((S)-pyrrolidin-2-yl)methanol (XI-a)
(S)-2-Tosyl-1-((S)-1-tritylpyrrolidin-2-yl)ethanol (XIII-a)
(R)-2-Tosyl-1-((R)-1-tritylpyrrolidin-2-yl)ethanol (XIII-b)

The chiral reagent reacts with a nucleic acid or modified nucleic acid to be an asymmetric auxiliary group. A nucleoside 3'-phosphoramidite derivative, which is an intermediate of manufacturing a stereocontrolled phosphorus atom-modified oligonucleotide derivative, is obtained by chiral reagent reacting with a nucleic acid or modified nucleic acid.

The second aspect of the invention relates to a nucleoside 3'-phosphoramidite derivative which is represented by formula (Va) or (Vb). The compounds of formula (Va) and (Vb) are known as monomers that are used in synthesizing oligonucleotide derivatives. These compounds are also known as oxazaphospholidine monomers. The sugar moieties of the compounds represented by formula (Vb) are known as BNA and LNA (when $R^3$ is a methylene group).

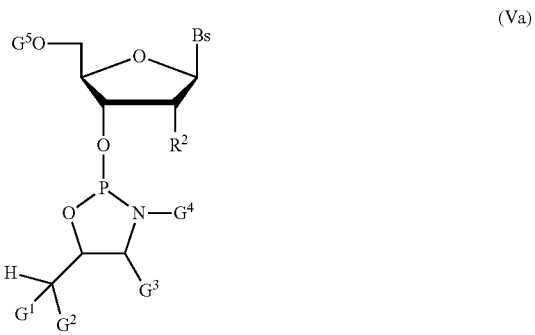

(Va)

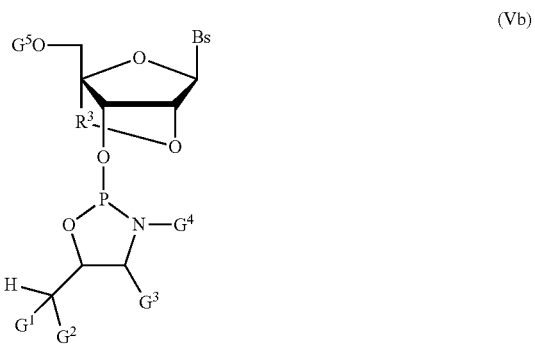

(Vb)

In the formula (Va) and (Vb), $G^1$ to $G^4$ are same as above, $G^5$ is a protective group of the hydroxyl group, and Bs is a group selected from the groups represented by formula (VI) to (XI) or derivatives thereof.

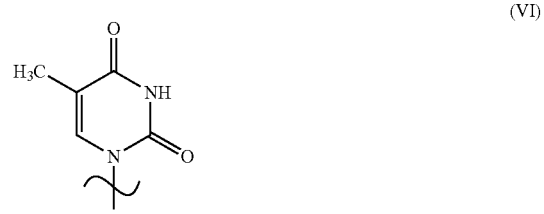

(VI)

-continued (VII)
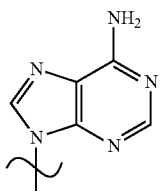

(VIII)
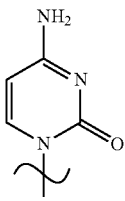

(IX)
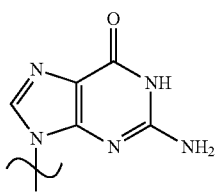

(X)
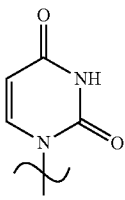

(XI)
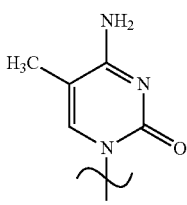

Examples of Bs are an adenine, a thymine, a cytosine, a guanine, an uracil, a 5-methylcytosine, or derivative thereof.

$R^2$ is hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^b$, wherein $R^b$ is a blocking moiety.

$Y^1$ is O, $NR^d$, S, or Se.

$R^d$ is independently hydrogen, alkyl, alkenyl, alkynyl, aryl, acyl, substituted silyl, carbamate, —$P(O)(R^e)_2$, or —$HP(O)(R^e)$.

$R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^+$, $Li^+$, or $K^+$.

$Y^2$ is O, $NR^d$, or S.

Preferred examples of alkyl are $C_{1-10}$ alkyl group, preferred examples of alkenyl are $C_{2-10}$ alkenyl, preferred examples of alkynyl are $C_{2-10}$ alkynyl, preferred examples of aryl are $C_{6-14}$ aryl, and preferred examples of heteroaryl are $C_{6-14}$ heteroaryl.

$R^3$ is a group represented by —$CH_2$—, —$(CH_2)_2$—, —$CH_2NH$—, or —$CH_2N(CH_3)$—.

Examples of $G^5$ the trityl, 4-monomethoxytrityl, 4,4'-dimethoxytrityl, 4,4',4''-trimethoxytrityl, 9-phenylxanthin-9-yl (Pixyl) and 9-(p-methoxyphenyl)xanthin-9-yl (MOX).

Bs is an adenine, a thymine, a cytosine, a guanine, or derivative thereof. Bs is a nucleobase or a modified nucleobase. The examples of the derivatives are that disclosed in JP 2005-89441 A and are represented as follows.

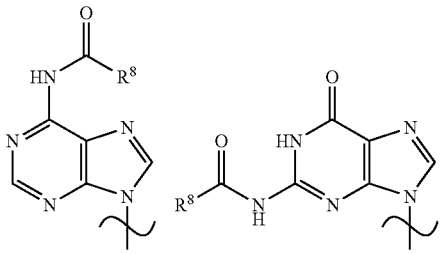

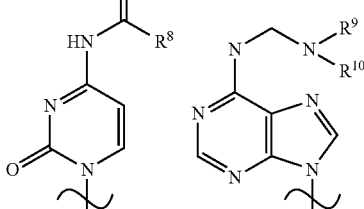

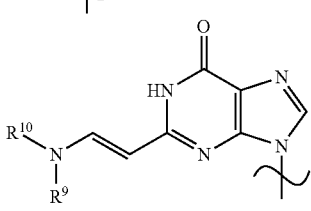

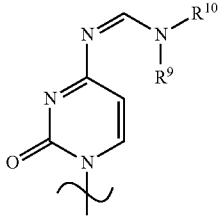

In the above formula, each of $R^8$ to $R^{10}$ is independently $C_{1-10}$ alkyl, $C_6$-$C_{10}$ aryl, $C_6$-$C_{10}$ aralkyl, or $C_6$-$C_{10}$ aryloxyalkyl. Preferred examples of $R^8$ are methyl, isopropyl, phenyl, benzyl, and phenoxymethyl. Preferred examples of $R^9$ and $R^{10}$ are $C_{1-4}$ alkyl group.

A preferred embodiment of the second aspect is that the nucleoside 3'-phosphoramidite derivative is represented by formula (Va') or (Vb').

(Va')
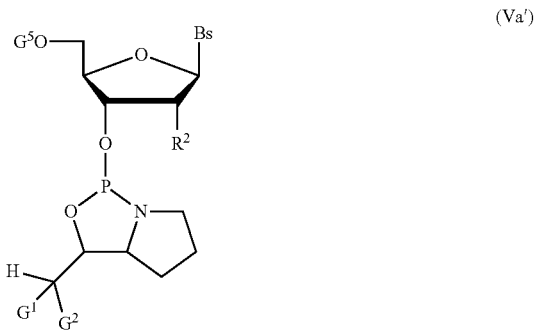

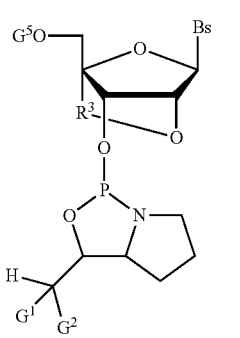

(Vb')

In the formula (Va') and (Vb'), $G^1$, $G^2$, $G^5$, Bs, $R^2$, and $R^3$ are same as above. The nucleoside 3'-phosphoramidite derivative is a chiral monomer which is used to produce stereocontrolled phosphorus atom-modified nucleotides and oligonucleotide derivatives.

Preferred examples of the nucleoside 3'-phosphoramidite derivatives are represented by the formula 1a, 1b, 2a, 2b, 3a, 3b, 4a, 4b, 5a, 5b, 6a, 6b, 7a, 7b, 8a, 8b, 9a, 9b, 10a, 10b, 11a, 11b 12a, 12b, 13a, 13b, 14a, 14b, 15a, 15b, 16a, 16b, 17a, 17b, 18a, 18b, 19a, 19b, 20a, 20b, 21a, 21b, 22a, 22b, 23a, 23b, or 24a. These formulas are described at the Experimental section.

DMTr represents a 4,4'-dimethoxytrityl group and TOM represents a triisopropylsiloxymethyl group.

The examples of using the nucleoside 3'-phosphoramidite derivative are disclosed in, e.g., JP 2005-89441 A. By repeating steps of condensation and de-protection, it is possible to lengthen the chain of oligonucleotide derivatives as disclosed therein.

Formula of such an oligonucleotide derivative is shown in formula (X).

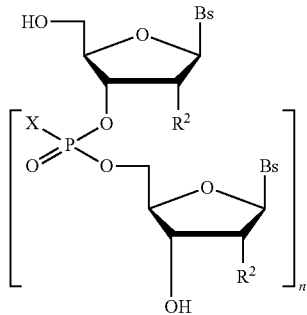

(X)

In the formula (X), X represents sulfide (=S), $C_{1-3}$ alkyl, $C_{1-3}$ alkoxy, $C_{1-3}$ alkylthio, $C_6$-$C_{10}$ aryl, $C_6$-$C_{10}$ aralkyl, or $C_6$-$C_{10}$ aryloxialkyl. Preferably, X represents sulfide (=S). "n" is an integer that represents 1 to 150, 1 to 100, 1 to 50, or 1 to 30. "n" may be preferably 2 to 100, preferably 10 to 100, preferably 10 to 50, and more preferably 15 to 30.

The third aspect of the invention relates to a method for synthesis of a stereocontrolled phosphorus atom-modified oligonucleotide derivative. First step is a step of reacting a molecule comprising an achiral H-phosphonate moiety, the first activating reagent and a chiral reagent or a salt thereof to form a monomer. The chiral reagent has chemical formula (I) or (I') and the monomer may be represented by formula (Va), (Vb), (Va'), or (Vb'). The monomer reacts with the second activating reagent and a nucleoside to form a condensed intermediate. Next step is a step of converting the condensed intermediate to the nucleic acid comprising a chiral X-phosphonate moiety. The method basically based on disclosure of WO 2010/064146 pamphlet. Namely, fundamental steps are disclosed as route A and route B therein. In the method the chiral reagent of the present invention is used.

First Scheme Relates to Synthesis of Chiral Oligos.

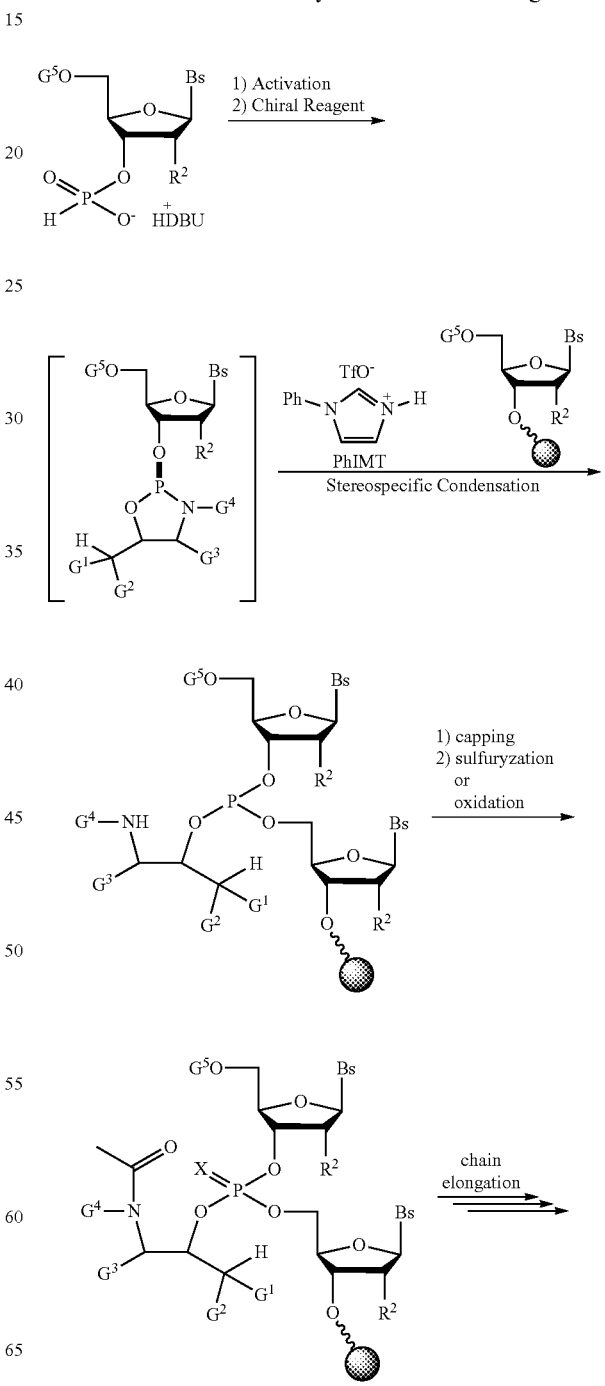

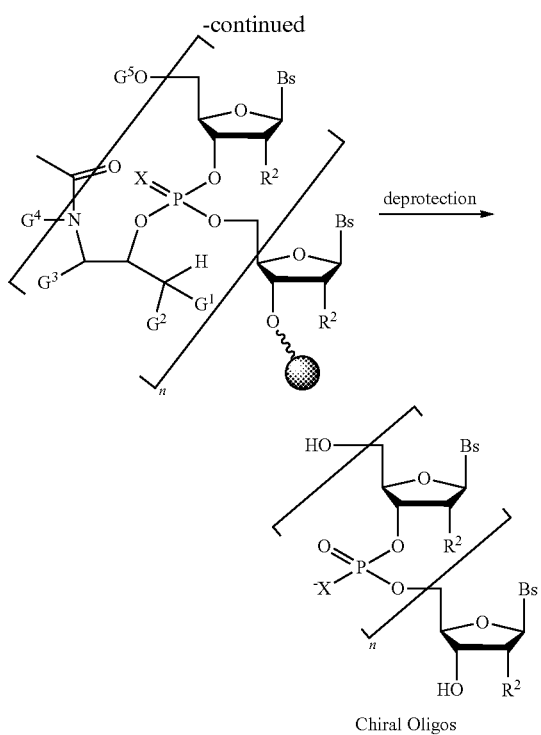

Chiral Oligos

Activation Step

An achiral H-phosphonate moiety is treated with the first activating reagent to form the first intermediate. In one embodiment, the first activating reagent is added to the reaction mixture during the condensation step. Use of the first activating reagent is dependent on reaction conditions such as solvents that are used for the reaction. Examples of the first activating reagent are phosgene, trichloromethyl chloroformate, bis(trichloromethyl)carbonate (BTC), oxalyl chloride, Ph$_3$PCl$_2$, (PhO)$_3$PCl$_2$, N,N'-bis(2-oxo-3-oxazolidinyl)phosphinic chloride (BopCl), 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP).

The example of achiral H-phosphonate moiety is a compound shown in the above Scheme. DBU represents 1,8-diazabicyclo[5.4.0]undec-7-ene. H$^+$DBU may be, for example, ammonium ion, alkylammonium ion, heteroaromatic iminium ion, or heterocyclic iminium ion, any of which is primary, secondary, tertiary or quaternary, or a monovalent metal ion.

Reacting with Chiral Reagent

After the first activation step, the activated achiral H-phosphonate moiety reacts with a chiral reagent, which is represented by formula (I) or (I'), to form a chiral intermediate of formula (Va), (Vb), (Va'), or (Vb').

Stereospecific Condensation Step

A chiral intermediate of Formula Va ((Vb), (Va'), or (Vb')) is treated with the second activating reagent and a nucleoside to form a condensed intermediate. The nucleoside may be solidified. Examples of the second activating reagent are 4,5-dicyanoimidazole (DCI), 4,5-dichloroimidazole, 1-phenylimidazolium triflate (PhIMT), benzimidazolium triflate (BIT), benztriazole, 3-nitro-1,2,4-triazole (NT), tetrazole, 5-ethylthiotetrazole (ETT), 5-benzylthiotetrazole (BTT), 5-(4-nitrophenyl)tetrazole, N-cyanomethylpyrrolidinium triflate (CMPT), N-cyanomethylpiperidinium triflate, N-cyanomethyldimethylammonium triflate. A chiral intermediate of Formula Va ((Vb), (Va'), or (Vb')) may be isolated as a monomer. Usually, the chiral intermediate of Va ((Vb), (Va'), or (Vb')) is not isolated and undergoes a reaction in the same pot with a nucleoside or modified nucleoside to provide a chiral phosphite compound, a condensed intermediate. In other embodiments, when the method is performed via solid phase synthesis, the solid support comprising the compound is filtered away from side products, impurities, and/or reagents.

Capping Step

If the final nucleic acid is larger than a dimer, the unreacted —OH moiety is capped with a blocking group and the chiral auxiliary in the compound may also be capped with a blocking group to form a capped condensed intermediate. If the final nucleic acid is a dimer, then the capping step is not necessary.

Modifying Step

The compound is modified by reaction with an electrophile. The capped condensed intermediate may be executed modifying step. In some embodiments of the method, the modifying step is performed using a sulfur electrophile, a selenium electrophile or a boronating agent. The preferred examples of modifying steps are step of oxidation and sulfurization.

In some embodiments of the method, the sulfur electrophile is a compound having one of the following formulas:

$$Z^1-S-S-Z^2, \text{ or } Z^1-S-V-Z^2. \qquad S_8 \text{ (Formula B)},$$

$Z^1$ and $Z^2$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^1$ and $Z^2$ are taken together to form a 3 to 8 membered alicyclic or heterocyclic ring, which may be substituted or unsubstituted; V is SO$_2$, O, or NR$^f$; and R$^f$ is hydrogen, alkyl, alkenyl, alkynyl, or aryl.

In some embodiments of the method, the sulfur electrophile is a compound of following Formula A, B, C, D, E, or F:

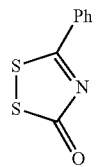

Formula A

S$_8$     Formula B

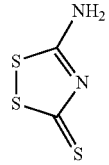

Formula C

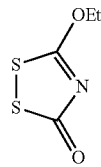

Formula D

-continued

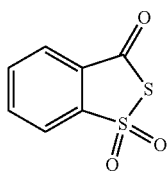
Formula E

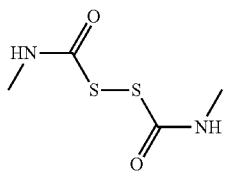
Formula F

In some embodiments of the method, the selenium electrophile is a compound having one of the following formulas:

$Z^3-Se-Se-Z^4$, or $Z^3-Se-V-Z^4$  Se (Formula G), $Z^3$ and $Z^4$ are independently alkyl, aminoalkyl, cycloalkyl, heterocyclic, cycloalkylalkyl, aryl, heteroaryl, alkyloxy, aryloxy, heteroaryloxy, acyl, amide, imide, or thiocarbonyl, or $Z^3$ and $Z^4$ are taken together to form a 3 to 8 membered alicyclic or heterocyclic ring, which may be substituted or unsubstituted; V is $SO_2$, S, O, or $NR^f$; and $R^f$ is hydrogen, alkyl, alkenyl, alkynyl, or aryl.

In some embodiments of the method, the selenium electrophile is a compound of Formula G, H, I, J, K, or L.

Se  Formula G

KSeCN  Formula H

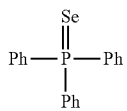
Formula I

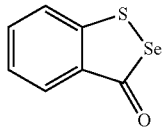
Formula J

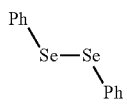
Formula K

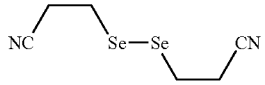
Formula L

In some embodiments of the method, the boronating agent is borane-N,N-diisopropylethylamine ($BH_3$ DIPEA), borane-pyridine ($BH_3$ Py), borane-2-chloropyridine ($BH_3$ CPy), borane-aniline ($BH_3$ An), borane-tetrahydrofurane ($BH_3$ THF), or borane-dimethylsulfide ($BH_3$ $Me_2S$).

In some embodiments of the method, the modifying step is oxidation step. Oxidation step is disclosed in, e.g., JP 2010-265304 A and WO2010/064146.

Chain Elongation Cycle and De-Protection Step

The capped condensed intermediate is deblocked to remove the blocking group at the 5'-end of the growing nucleic acid chain to provide a compound. The compound is optionally allowed to re-enter the chain elongation cycle to form a condensed intermediate, a capped condensed intermediate, a modified capped condensed intermediate, and a 5'-deprotected modified capped intermediate. Following at least one round of chain elongation cycle, the 5'-deprotected modified capped intermediate is further deblocked by removal of the chiral auxiliary ligand and other protecting groups, e.g., nucleobase, modified nucleobase, sugar and modified sugar protecting groups, to provide a nucleic acid. In other embodiments, the nucleoside comprising a 5'-OH moiety is an intermediate from a previous chain elongation cycle as described herein. In yet other embodiments, the nucleoside comprising a 5'-OH moiety is an intermediate obtained from another known nucleic acid synthetic method. In embodiments where a solid support is used, the phosphorus-atom modified nucleic acid is then cleaved from the solid support. In certain embodiments, the nucleic acids is left attached on the solid support for purification purposes and then cleaved from the solid support following purification.

Based on the present method, it is possible to use stable and commercially available materials as starting materials. It is possible to produce stereocontrolled phosphorus atom-modified oligonucleotide derivatives using an achiral starting material.

As shown in a working example, the method of the present invention does not cause degradations under the de-protection steps. Further the method does not require special capping agents to produce phosphorus atom-modified oligonucleotide derivatives.

The fourth aspect of the invention relates to a method for the synthesis of stereocontrolled phosphorus atom-modified oligonucleotide derivatives using a chiral monomer. The first step is reacting a nucleoside 3'-phosphoramidite derivative which is represented by formula (Va), (Vb), (Va'), or (Vb') with the second activating reagent and a nucleoside to form a condensed intermediate. The second step is converting the condensed intermediate to the nucleic acid comprising a chiral X-phosphonate moiety.

Second Scheme relates to synthesis of Chiral Oligos using a monomer of Formula Va ((Vb), (Va'), or (Vb')). The second Scheme based on the method disclosed in JP 2005-89441 A.

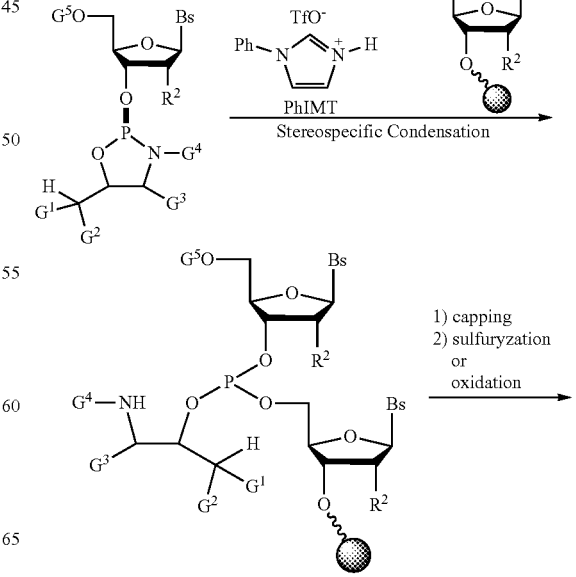

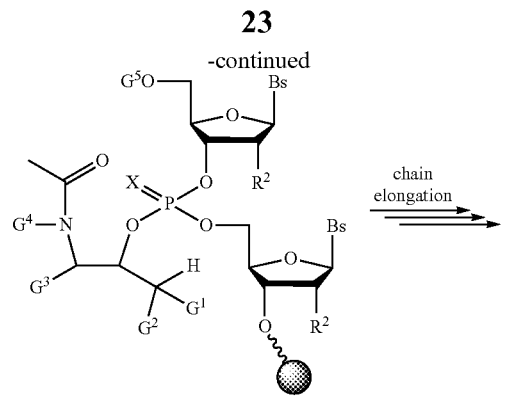

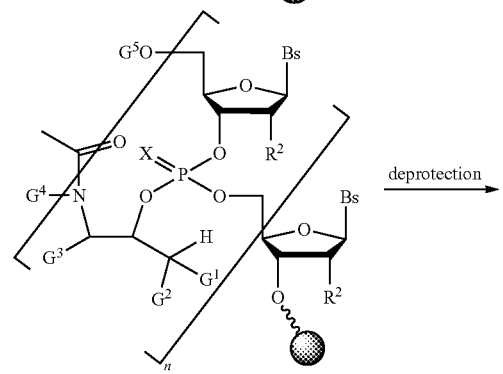

Chiral Oligos

The detailed conditions of the above scheme are similar to that of the first scheme. The starting material of formula Va (Vb), especially of formula Va' (or Vb'), is chemically stable. As shown in a working example, the method of the present invention does not cause degradations under the de-protection steps. Further the method does not require special capping agents to produce phosphorus atom-modified oligonucleotide derivatives.

Mechanism for the removal of auxiliaries is shown as follows:

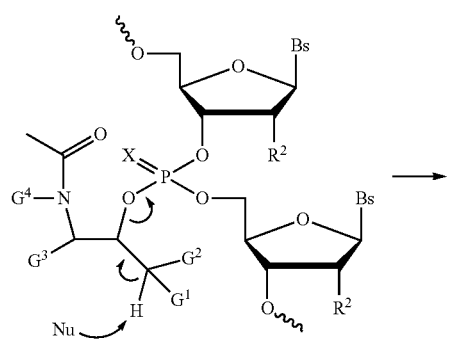

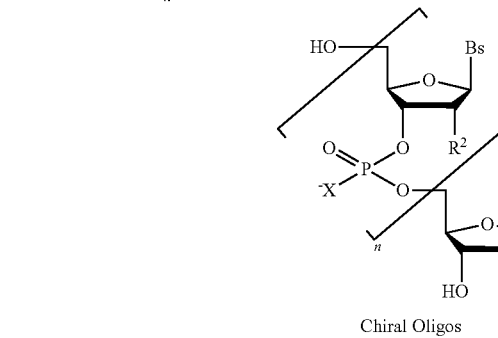

In the above scheme, Nu stands for Nucleophile. The above mechanism is thought to be different from the previous mechanism for the removal of auxiliaries.

EXAMPLES

Abbreviation ac: acetyl
bz: benzoyl
CSO: (1S)-(+)-(10-camphorsulfonyl)oxaziridine
DBU: 1,8-diazabicyclo[5.4.0]undec-7-ene
DCA: dichloroacetic acid
DCM: dichloromethane, $CH_2Cl_2$
DMTr: 4,4'-dimethoxytrityl
Tr: trityl, triphenylmethyl
MeIm: N-methylimidazole
NIS: N-iodosuccinimide
pac: phenoxyacetyl
Ph: phenyl
PhIMT: N-phenylimidazolium triflate
POS: 3-phenyl-1,2,4-dithiazoline-5-one
TBS: tert-butyldimethylsilyl
TBDPS: tert-butyldiphenylsilyl
TOM: triisopropylsiloxymethyl
TFA: trifluoroacetic acid Example 1

(S)-1-Tritylpyrrolidin-2-carbaldehyde (I-a)

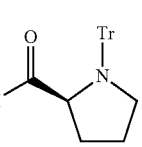

Compound I-a was synthesized from L-proline according to the procedure described in the literature (Guga, P. Curr. Top. Med. Chem. 2007, 7, 695-713.).

Example 2

(R)-1-Tritylpyrrolidin-2-carbaldehyde (I-b)

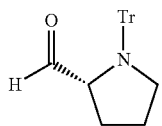

Compound I-b was synthesized from D-proline in a similar manner to compound I-a.

Example 3

(S)-2-(Methyldiphenylsilyl)-1-((S)-1-tritylpyrrolidin-2-yl)ethanol (II-a)

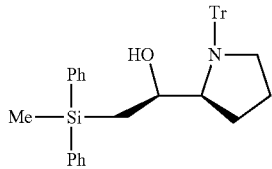

To a solution of methyldiphenylsilylmethyl magnesium chloride in THF prepared from chloromethyldiphenylmethylsilane (4.02 g, 16.3 mmol) and magnesium (402 mg, 16.3 mmol) in THF (14 mL) was added I-a (2.79 g, 8.14 mmol) in THF (30 mL) solution with ice cooling. After stirring for 1.5 h with ice cooling, the mixture warmed to room temperature and continued stirring for 30 min. Saturated aqueous $NH_4Cl$ (100 mL) was added to the reaction mixture at 0 degrees C., and extraction was performed with diethylether (100 mL) for three times. The combined extract was dried over $Na_2SO_4$, filtered and concentrated under reduced pressure. The residue was chromatographed on silica gel afforded II-a as a colorless foam (3.91 g, 87%).

$^1$H NMR (300 MHz, $CDCl_3$) d 7.48-7.08 (25H, m), 4.33-4.23 (1H, m), 3.16-2.89 (3H, m), 2.84 (1H, brs), 1.70-1.54 (1H, m), 1.35 (1H, dd, J=14.7, 6.3 Hz), 1.10 (1H, dd, J=14.7, 8.1 Hz), 1.18-1.05 (1H, m), 1.04-0.90 (1H, m), 0.34 (3H, s), −0.17−−0.36 (1H, m).

Example 4

(S)-2-(Methyldiphenylsilyl)-1-((S)-pyrrolidin-2-yl)ethanol (III-a)

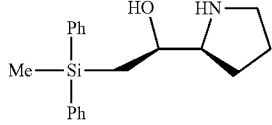

II-a (3.91 g, 7.06 mmol) was dissolved in 3% DCA in DCM (70 mL), and stirred for 10 min at room temperature. To the mixture, 1M NaOH (200 mL) was added, and extraction was performed with DCM (100 mL) for three times. The combined extract was dried over $Na_2SO_4$, filtered and concentrated under reduced pressure. The residue was chromatographed on silica gel afforded III-a as a light yellow oil (1.99 g, 90%).

$^1$H NMR (300 MHz, $CDCl_3$) d 7.57-7.52 (5H, m), 7.38-7.33 (5H, m), 3.77 (1H, ddd, J=8.9, 5.4, 3.5 Hz), 3.01 (1H, dt, J=7.4, 3.6 Hz), 2.97-2.79 (2H, m), 2.27 (2H, brs), 1.76-1.53 (4H, m), 1.38 (1H, dd, J=15.0, 9.0 Hz), 1.24 (1H, dd, J=15.0, 5.4 Hz), 0.65 (3H, s); $^{13}$C NMR (100.4 MHz, $CDCl_3$) d 137.4, 137.1, 134.6, 134.5, 129.1, 127.8, 69.5, 64.1, 47.0, 25.8, 24.0, 19.6, −3.4. MALDI TOF-MS m/z Calcd for $C_{19}H_{26}NOSi$ [M+H]$^+$ 312.18, found 312.06.

Example 5

(R)-2-(Methyldiphenylsilyl)-1-((R)-1-tritylpyrrolidin-2-yl)ethanol (II-b)

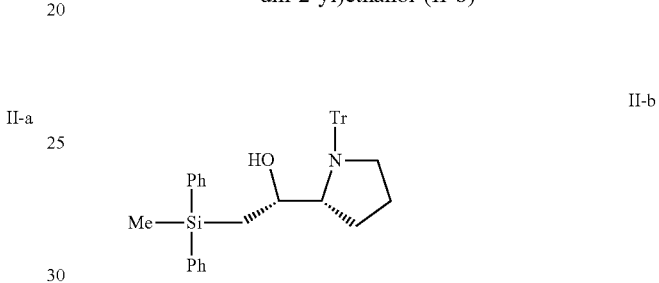

Compound II-b was obtained by using I-b instead of I-a in a similar manner to compound II-a.

$^1$H NMR (300 MHz, $CDCl_3$) d 7.48-7.12 (25H, m), 4.33-4.24 (1H, m), 3.16-2.89 (3H, m), 2.86 (1H, brs), 1.69-1.52 (1H, m), 1.35 (1H, dd, J=14.4, 6.0 Hz), 1.10 (1H, dd, J=14.4, 8.4 Hz), 1.18-1.05 (1H, m), 1.03-0.89 (1H, m), 0.33 (3H, s), −0.19−−0.39 (1H, m); $^{13}$C NMR (75.5 MHz, $CDCl_3$) d 144.5, 137.5, 136.8, 134.6, 134.3, 129.8, 129.0, 127.8, 127.7, 127.4, 126.1, 77.9, 71.7, 65.1, 53.5, 25.0, 24.8, 19.6, −4.0. MALDI TOF-MS m/z Calcd for $C_{38}H_{40}NOSi$ [M+H]$^+$ 554.29, found 554.09.

Example 6

(R)-2-(Methyldiphenylsilyl)-1-((R)-1-pyrrolidin-2-yl)ethanol (III-b)

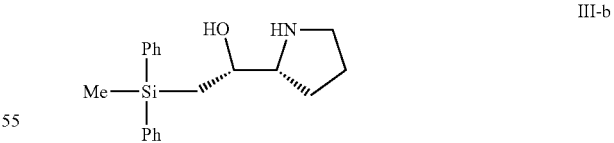

Compound III-b was obtained by using II-b instead of II-a in a similar manner to compound III-a.

$^1$H NMR (300 MHz, $CDCl_3$) d 7.58-7.52 (5H, m), 7.38-7.33 (5H, m), 3.78 (1H, ddd, J=9.0, 5.1, 3.6 Hz), 3.00 (1H, dt, J=7.4, 3.3 Hz), 2.97-2.78 (2H, m), 2.19 (2H, brs), 1.76-1.53 (4H, m), 1.38 (1H, dd, J=14.6, 9.0 Hz), 1.24 (1H, dd, J=14.6, 5.1 Hz), 0.66 (3H, s); $^{13}$C NMR (75.5 MHz, $CDCl_3$) d 137.5, 137.1, 134.5, 134.4, 129.0, 127.7, 69.2, 64.2, 46.9, 25.8, 24.0, 19.7, −3.4. MALDI TOF-MS m/z Calcd for $C_{19}H_{26}NOSi$ [M+H]$^+$ 312.18, found 312.09.

Example 7

(S)-2-(Trimethylsilyl)-1-((S)-1-tritylpyrrolidin-2-yl)ethanol (IV-a)

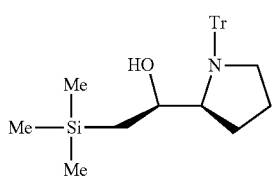

IV-a

Compound IV-a was obtained by using "chloromethyltrimethylsilane" instead of "chloromethyldiphenylmethylsilane" in a similar manner to compound II-a.

$^1$H NMR (300 MHz, CDCl$_3$) d 7.58-7.51 (5H, m), 7.31-7.14 (10H, m), 4.13 (1H, dt, J=7.5, 3.0 Hz), 3.39-3.31 (1H, m), 3.20-2.99 (2H, m), 2.84 (1H, s), 1.74-1.57 (1H, m), 1.29-1.10 (2H, m), 0.74 (1H, dd, J=14.4, 7.2 Hz), 0.46 (1H, dd, J=14.4, 7.2 Hz), −0.15 (9H, s). MALDI TOF-MS m/z Calcd for C$_{28}$H$_{36}$NOSi [M+H]$^+$ 430.26, found 430.09.

Example 8

(S)-2-(Trimethylsilyl)-1-((S)-1-pyrrolidin-2-yl)ethanol (V-a)

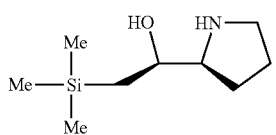

V-a

Compound V-a was obtained by using IV-a instead of II-a in a similar manner to compound III-a.

$^1$H NMR (300 MHz, CDCl$_3$) d 3.76 (1H, ddd, J=8.8, 5.7, 3.3 Hz), 3.08 (1H, dt, J=7.8, 3.3 Hz), 3.02-2.87 (2H, m), 2.48 (2H, brs), 1.81-1.58 (4H, m), 0.83 (1H, dd, J=14.7, 8.7 Hz), 0.68 (1H, dd, J=14.7, 6.0 Hz), 0.05 (9H, s); $^{13}$C NMR (75.5 MHz, CDCl$_3$) d 69.6, 64.3, 46.9, 25.8, 23.9, 22.0, −0.8. MALDI TOF-MS m/z Calcd for C$_9$H$_{22}$NOSi [M+H]$^+$ 188.15, found 188.00.

Example 9

(R)-2,2-Diphenyl-1-((S)-1-tritylpyrrolidin-2-yl)ethanol (VI-a)

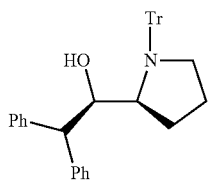

VI-a

To a solution of diphenylmethane (6.7 mL, 40 mmol) in anhydrous THF (36 mL), n-BuLi (1.67M solution of Hexane, 24 mL, 40 mmol) was added dropwise at room temperature and stirred for 1 h. To the mixture, I-a (3.41 g, 10 mmol), which was dried by repeated coevaporations with toluene, in anhydrous THF (40 mL) was slowly added at 0 degrees C., and continued stirring for 45 min. A saturated NH$_4$Cl aqueous solution (100 mL) and Et$_2$O (100 mL) were then added, and the organic layer was separated and the aqueous layer was extracted with Et$_2$O (2×100 mL). The organic layer were combined, dried over Na$_2$SO$_4$, filtered and concentrated under reduced pressure. The residue was purified by chromatography on silica gel to afford VI-a (1.41 g, 28%) as white foam.

$^1$H NMR (300 MHz, CDCl$_3$) d 7.45-7.01 (23H, m), 6.67-6.61 (2H, m), 4.80 (1H, d, J=10.8 Hz), 3.63 (1H, d, J=10.8 Hz), 3.36-3.27 (1H, m), 3.23-3.09 (1H, m), 3.02-2.89 (1H, m), 2.66 (1H, s), 1.90-1.75 (1H, m), 1.32-1.04 (2H, m), 0--0.18 (1H, m).

Example 10

(R)-2,2-Diphenyl-1-((S)-pyrrolidin-2-yl)ethanol (VII-a)

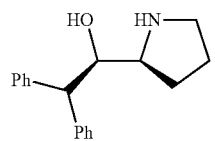

VII-a

Compound VII-a was obtained by using VI-a instead of II-a in a similar manner to compound III-a.

$^1$H NMR (300 MHz, CDCl$_3$) d 7.44-7.38 (2H, m), 7.33-7.14 (8H, m), 4.46 (1H, dd, J=9.9, 3.3 Hz), 3.91 (1H, d, J=9.9 Hz), 3.02-2.88 (2H, m), 2.81-2.69 (1H, m), 2.52 (2H, brs), 1.88-1.56 (4H, m); $^{13}$C NMR (75.5 MHz, CDCl$_3$) d 142.3, 142.0, 128.6, 128.5, 128.4, 128.2, 126.5, 126.4, 73.5, 60.1, 55.8, 46.6, 25.8, 23.4. MALDI TOF-MS m/z Calcd for C$_{18}$H$_{22}$NO [M+H]$^+$ 268.17, found 268.06.

Example 11

(S)-2,2-Diphenyl-1-((R)-1-tritylpyrrolidin-2-yl)ethanol (VI-b)

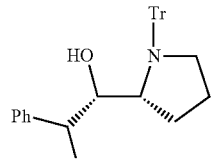

VI-b

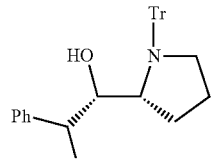

Compound VI-b was obtained by using I-b instead of I-a in a similar manner to compound VI-a.

$^1$H NMR (300 MHz, CDCl$_3$) d 7.44-7.37 (6H, m), 7.30-7.01 (17H, m), 6.66-6.61 (2H, m), 4.80 (1H, d, J=10.8 Hz), 3.63 (1H, d, J=10.8 Hz), 3.36-3.28 (1H, m), 3.22-3.09 (1H, m), 3.01-2.89 (1H, m), 2.66 (1H, s), 1.90-1.75 (1H, m), 1.29-1.04 (2H, m), 0.00--0.19 (1H, m); $^{13}$C NMR (75.5 MHz,

CDCl₃) d 144.2, 142.9, 141.6, 130.0, 128.5, 128.4, 127.9, 127.8, 127.4, 126.4, 126.2, 77.9, 75.9, 61.9, 55.4, 53.4, 24.7, 24.5. MALDI TOF-MS m/z Calcd for C₃₇H₃₆NO [M+H]⁺ 510.28, found 510.11.

Example 12

(S)-2,2-Diphenyl-1-((R)-pyrrolidin-2-yl)ethanol (VII-b)

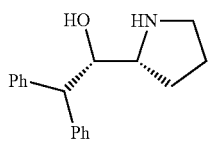

VII-b

Compound VII-b was obtained by using VI-b instead of VI-a in a similar manner to compound VII-a.

¹H NMR (300 MHz, CDCl₃) d 7.45-7.14 (10H, m), 4.45 (1H, dd, J=9.9, 3.3 Hz), 3.91 (1H, d, J=9.9 Hz), 3.00-2.89 (2H, m), 2.82-2.71 (1H, m), 2.40 (2H, brs), 1.87-1.55 (4H, m); ¹³C NMR (75.5 MHz, CDCl₃) d 142.3, 142.0, 128.5, 128.3, 128.1, 126.3, 126.2, 73.4, 60.1, 55.9, 46.5, 25.8, 23.5. MALDI TOF-MS m/z Calcd for C₁₈H₂₂ NO [M+H]⁺ 268.17, found 268.03.

Example 13

(R)-2-(4-Nitrophenyl)-1-((S)-1-tritylpyrrolidin-2-yl)ethanol (VIII-a)

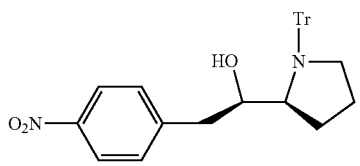

VIII-a

Compound VIII-a was obtained by using "4-nitrobenzyl-chloride" instead of "diphenylmethane" in a similar manner to compound VI-a.

¹H NMR (300 MHz, CDCl₃) d 8.09-8.03 (2H, m), 7.49-7.43 (6H, m), 7.28-7.09 (11H, m), 4.23 (1H, ddd, J=8.3, 5.6, 3.0 Hz), 3.43-3.33 (1H, m), 3.23-3.11 (1H, m), 3.07-2.96 (1H, m), 2.83 (1H, brs), 2.74 (1H, dd, J=13.8, 8.4 Hz), 2.49 (1H, dd, J=13.8, 5.1 Hz), 1.83-1.67 (1H, m), 1.41-1.17 (2H, m), 0.27-0.08 (1H, m); ¹³C NMR (75.5 MHz, CDCl₃) d 147.3, 146.3, 144.3, 129.8, 129.6, 127.5, 126.3, 123.4, 77.9, 74.8, 63.5, 53.2, 39.5, 25.0, 24.9. MALDI TOF-MS m/z Calcd for C₃₁H₃₁N₂O₃ [M+H]⁺ 479.23, found 479.08.

Example 14

(R)-2-(4-Nitrophenyl)-1-((S)-pyrrolidin-2-yl)ethanol (IX-a)

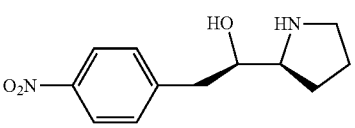

IX-a

Compound IX-a was obtained by using VIII-a instead of VI-a in a similar manner to compound VII-a.

¹H NMR (300 MHz, CDCl₃) d 8.15 (2H, d, J=8.7 Hz), 7.42 (2H, d, J=8.7 Hz), 3.86-3.79 (1H, m), 3.16-3.07 (1H, m), 2.99-2.68 (6H, m), 1.84-1.68 (4H, m); ¹³C NMR (75.5 MHz, CDCl₃) d 147.4, 146.2, 129.9, 123.2, 72.4, 62.0, 46.6, 40.4, 25.7, 24.4. MALDI TOF-MS m/z Calcd for C₁₂H₁₇N₂O₃ [M+H]⁺ 237.12, found 237.01.

Example 15

(S)-2-(4-Nitrophenyl)-1-((R)-1-tritylpyrrolidin-2-yl)ethanol (VIII-b)

VIII-b (structure)

Compound VIII-b was obtained by using I-b instead of I-a in a similar manner to compound VIII-a.

¹H NMR (300 MHz, CDCl₃) d 8.09-8.04 (2H, m), 7.49-7.43 (6H, m), 7.28-7.09 (11H, m), 4.22 (1H, ddd, J=8.4, 5.6, 3.0 Hz), 3.43-3.33 (1H, m), 3.24-3.10 (1H, m), 3.08-2.94 (1H, m), 2.81 (1H, brs), 2.75 (1H, dd, J=14.0, 8.1 Hz), 2.49 (1H, dd, J=14.0, 5.1 Hz), 1.81-1.67 (1H, m), 1.40-1.16 (2H, m), 0.26-0.09 (1H, m); ¹³C NMR (75.5 MHz, CDCl₃) d 147.3, 144.3, 129.8, 129.6, 129.4, 126.3, 123.5, 77.9, 74.8, 63.5, 53.2, 39.5, 25.0, 24.9. MALDI TOF-MS m/z Calcd for C₃₁H₃₁N₂O₃ [M+H]⁺ 479.23, found 479.08.

Example 16

(S)-2-(4-Nitrophenyl)-1-((R)-pyrrolidin-2-yl)ethanol (IX-b)

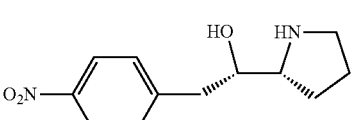

IX-b

Compound IX-b was obtained by using VIII-b instead of VIII-a in a similar manner to compound IX-a.

¹H NMR (300 MHz, CDCl₃) d 8.19-8.13 (2H, m), 7.45-7.39 (2H, m), 3.83 (1H, ddd, J=7.7, 5.4, 3.9 Hz), 3.14 (1H, dt, J=7.7, 3.9 Hz), 3.01-2.87 (2H, m), 2.83 (1H, d, J=3.3 Hz), 2.81 (1H, s), 2.62 (2H, brs), 1.79-1.72 (4H, m); $^{13}$C NMR (75.5 MHz, CDCl$_3$) d 147.3, 146.5, 130.0, 123.5, 72.7, 61.7, 46.7, 40.1, 25.8, 24.2. MALDI TOF-MS m/z Calcd for C$_{12}$H$_{17}$N$_2$O$_3$ [M+H]$^+$ 237.12, found 237.02.

Example 17

(R)-(9H-Fluoren-9-yl)((S)-1-tritylpyrrolidin-2-yl)methanol (X-a)

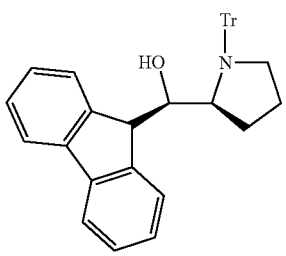

X-a

Compound X-a was obtained by using "fluorene" instead of "diphenylmethane" in a similar manner to compound VI-a.

$^1$H NMR (300 MHz, CDCl$_3$) d 7.70 (1H, d, J=7.5 Hz), 7.66 (1H, d, J=7.8 Hz), 7.55 (2H, d, J=7.5 Hz), 7.44-7.09 (18H, m), 6.87-6.62 (1H, m), 4.55-4.48 (1H, m), 4.06 (1H, d, J=7.5 Hz), 3.43-3.34 (1H, m), 3.18-3.06 (1H, m), 2.98-2.88 (1H, m), 2.85 (1H, brs), 1.42-1.24 (1H, m), 1.18-1.04 (1H, m), 0.53-0.39 (1H, m), −0.02-−0.20 (1H, m); MALDI TOF-MS Calcd for C$_{37}$H$_{34}$NO [M+H]$^+$ 508.26, found 508.12.

Example 18

(R)-(9H-Fluororen-9-yl)((S)-pyrrolidin-2-yl)methanol (XI-a)

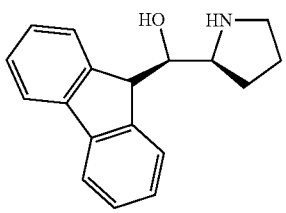

XI-a

Compound XI-a was obtained by using X-a instead of II-a in a similar manner to compound III-a.

$^1$H NMR (300 MHz, CDCl$_3$) d 7.76 (2H, d, J=7.5 Hz), 7.68 (2H, t, J=8.0 Hz), 7.43-7.35 (2H, m), 7.34-7.25 (2H, m), 4.28 (1H, d, J=6.3 Hz), 4.03 (1H, dd, J=6.5, 4.2 Hz), 3.19-3.11 (1H, m), 2.97-2.88 (1H, m), 2.86-2.76 (1H, m), 2.02 (2H, brs), 1.77-1.53 (3H, m), 1.38-1.23 (1H, m); MALDI TOF-MS m/z Calcd for C$_{18}$H$_{20}$NO [M+H]$^+$ 266.15, found 266.04.

Example 19

(S)-2-Tosyl-1-((S)-1-tritylpyrrolidin-2-yl)ethanol (XII-a)

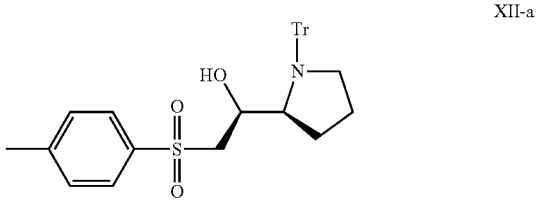

XII-a

Compound XII-a was obtained by using "chloromethyl p-tolyl sulfone" instead of "chloromethyldiphenylmethylsilane" in a similar manner to compound II-a.

$^1$H NMR (600 MHz, CDCl$_3$) d 7.66 (2H, d, J=8.4 Hz), 7.48-7.44 (6H, m), 7.35 (2H, d, J=7.2 Hz), 7.21-7.13 (9H, m), 4.39-4.36 (1H, m), 3.33 (1H, s), 3.24-3.20 (1H, m), 3.19-3.10 (2H, m), 2.98-2.92 (2H, m), 2.49 (3H, s), 1.55-1.49 (1H, m), 1.33-1.26 (1H, m), 1.12-1.04 (1H, m), 0.22-0.14 (1H, m); $^{13}$C NMR (150.9 MHz, CDCl$_3$) d 144.6, 144.5, 136.3, 129.9, 129.5, 128.1, 127.5, 126.2, 78.0, 69.1, 63.9, 60.2, 52.6, 25.5, 24.7, 21.7.

Example 20

(S)-2-Tosyl-1-((S)-1-tritylpyrrolidin-2-yl)ethanol (XIII-a)

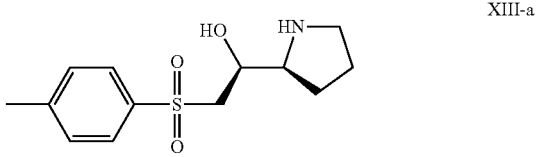 [SMILES: Cc1ccc(S(=O)(=O)C[C@@H](O)[C@@H]2CCCN2)cc1]

XIII-a

Compound XIII-a was obtained by using XII-a instead of II-a in a similar manner to compound III-a.

$^1$H NMR (600 MHz, CDCl$_3$) d 7.82 (2H, d, J=8.4 Hz), 7.37 (2H, d, J=8.4 Hz), 4.01 (1H, ddd, J=12.0, 5.1, 3.0 Hz), 3.32 (1H, dd, J=14.4, 3.0 Hz), 3.25 (1H, dd, J=14.4, 9.0 Hz), 3.16 (1H, dt, J=7.8, 5.1 Hz), 2.90-2.82 (2H, m), 2.46 (3H, s), 2.04 (2H, brs), 1.78-1.63 (3H, m), 1.62-1.55 (1H, m); $^{13}$C NMR (150.9 MHz, CDCl$_3$) d 144.5, 136.7, 129.7, 127.7, 67.4, 61.8, 60.1, 46.7, 25.7, 21.4. MALDI TOF-MS m/z Calcd for C$_{13}$H$_{20}$NO$_3$S [M+H]$^+$ 270.12, found 270.04.

Example 2

(R)-2-Tosyl-1-((R)-1-tritylpyrrolidin-2-yl)ethanol (XII-b)

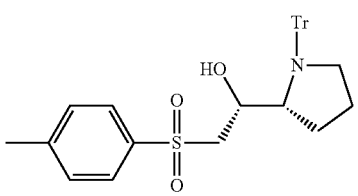

Compound XII-b was obtained by using I-b instead of I-a in a similar manner to compound XII-a.

$^1$H NMR (600 MHz, CDCl$_3$) d 7.66 (2H, d, J=8.4 Hz), 7.47-7.44 (6H, m), 7.35 (2H, d, J=7.8 Hz), 7.21-7.13 (9H, m), 4.37 (1H, dt, J=8.6, 2.4 Hz), 3.33 (1H, s), 3.23-3.20 (1H, m), 3.19-3.12 (2H, m), 2.98-2.92 (2H, m), 2.49 (3H, s), 1.56-1.49 (1H, m), 1.32-1.26 (1H, m), 1.11-1.03 (1H, m), 0.23-0.15 (1H, m); $^{13}$C NMR (150.9 MHz, CDCl$_3$) d 144.6, 144.5, 136.3, 129.9, 129.6, 128.1, 127.6, 126.2, 78.0, 69.1, 63.9, 60.2, 52.6, 25.5, 24.7, 21.7.

Example 21

(R)-2-Tosyl-1-((R)-1-tritylpyrrolidin-2-yl)ethanol (XIII-b)

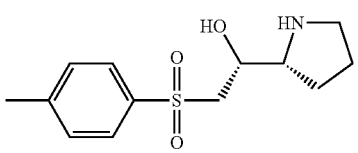

Compound XIII-b was obtained by using XII-b instead of XII-a in a similar manner to compound XIII-a.

$^1$H NMR (600 MHz, CDCl$_3$) d 7.82 (2H, d, J=8.4 Hz), 7.37 (2H, d, J=8.4 Hz), 4.01 (1H, ddd, J=9.0, 5.1, 3.0 Hz), 3.32 (1H, dd, J=14.4, 3.0 Hz), 3.25 (1H, dd, J=14.4, 9.0 Hz), 3.17 (1H, dt, J=7.2, 5.1 Hz), 2.89-2.83 (2H, m), 2.46 (3H, s), 2.04 (2H, brs), 1.79-1.64 (3H, m), 1.62-1.55 (1H, in); $^{13}$C NMR (150.9 MHz, CDCl$_3$) d 144.8, 136.6, 129.8, 127.9, 67.7, 61.8, 60.1, 46.8, 25.9, 25.8, 21.6. MALDI TOF-MS m/z Calcd for C$_{13}$H$_{20}$NO$_3$S [M+H]$^+$ 270.12, found 270.05.

Example 22

Oxazaphospholidine Monomer 3a

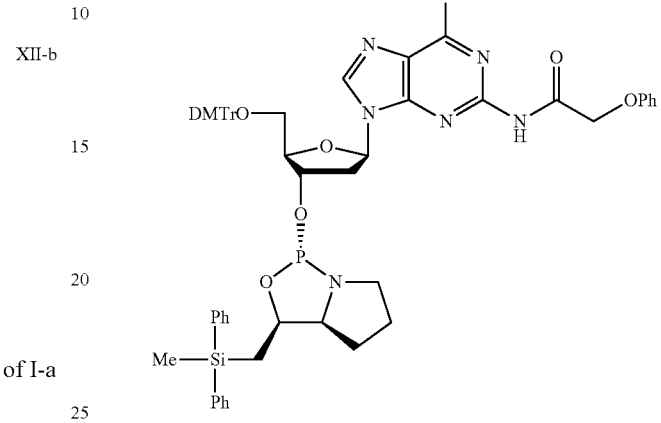

III-a (560 mg, 1.80 mmol) were dried by repeated coevaporations with dry toluene and dissolved in dry diethylether (0.90 mL) under argon. N-Methylmorpholine (400 mL, 3.60 mmol) was added to the solution, and the resultant solution was added dropwise to a solution of PCl$_3$ (160 mL, 1.80 mmol) in dry diethylether (0.90 mL) at 0 degrees C. under argon with stirring. The mixture was then allowed to warm to room temperature and stirred for 30 min. The resultant N-methylmorpholine hydrochloride was removed by filtration under nitrogen, and the filtrate was concentrated to dryness under reduced pressure to afford crude 2-chloro-1,3,2-oxazaphospholidine derivative. The crude materials were dissolved in freshly distilled THF (3.6 mL) to make 0.5 M solutions, which were used to synthesize the nucleoside 3'-O-oxazaphospholidines without further purification. 5'-O-(DMTr)-2-N-(phenoxyacetyl)-6-O-(cyanoethyl) guanosine (636 mg, 0.84 mmol) was dried by repeated coevaporations with dry toluene, and dissolved in freshly distilled THF (2.5 mL) under argon. Et$_3$N (0.58 mL, 4.2 mmol) was added, and the mixture was cooled to −78 degrees C. A 0.5 M solution of the corresponding crude 2-chloro-1,3,2-oxazaphospholidine derivative in freshly distilled THF (3.6 mL, 1.80 mmol) was added dropwise via a syringe, and the mixture was stirred for 15 min at room temperature. A saturated NaHCO$_3$ aqueous solution (70 mL) and CHCl$_3$ (70 mL) were then added, and the organic layer was separated and washed with saturated NaHCO$_3$ aqueous solutions (2×70 mL). The combined aqueous layers were back-extracted with CHCl$_3$ (70 mL). The organic layers were combined, dried over Na$_2$SO$_4$, filtered and concentrated under reduced pressure. The residue was purified by chromatography on silica gel to afford 3a (829 mg, 90%) as a white foam.

$^1$H NMR (300 MHz, CDCl$_3$) d 8.77 (1H, brs), 7.99 (1H, s), 7.54-6.98 (24H, m), 6.81-6.73 (4H, m), 6.35 (1H, dd, J=8.0, 6.3 Hz), 4.89-4.73 (4H, m), 4.68 (2H, brs), 4.05-3.98 (1H, m), 3.75 (6H, s), 3.62-3.46 (1H, m), 3.41-3.20 (3H, m), 3.18-3.04 (1H, m), 3.08 (2H, t, J=6.6 Hz), 2.58-2.36 (2H, m), 1.94-1.59 (2H, m), 1.56 (1H, dd, J=15.0, 8.7 Hz), 1.43 (1H, dd, J=15.0, 5.7 Hz), 1.33-1.16 (2H, m), 0.62 (3H, s); $^{31}$P NMR (121.5 MHz, CDCl$_3$) d 153.5 (1P, s).

Example 23

Oxazaphospholidine Monomer 3b

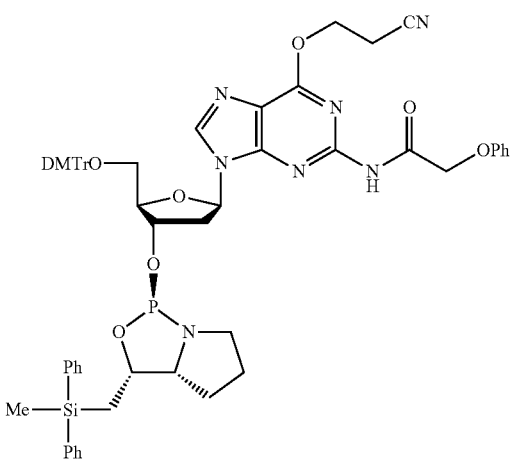

Compound 3b was obtained by using III-b instead of III-a in a similar manner to compound 3a.

$^1$H NMR (300 MHz, CDCl$_3$) d 8.80 (1H, brs), 7.96 (1H, s), 7.54-6.96 (24H, m), 6.79-6.71 (4H, m), 6.19 (1H, t, J=6.6 Hz), 4.90-4.73 (4H, m), 4.66 (2H, brs), 4.16-4.08 (1H, m), 3.76 (6H, s), 3.60-3.36 (2H, m), 3.29 (1H, d, J=3.9 Hz), 3.27-3.12 (2H, m), 3.09 (2H, t, J=6.6 Hz), 2.59-2.46 (1H, m), 2.07-1.97 (1H, m), 1.94-1.41 (5H, m), 1.36-1.18 (1H, m), 0.65 (3H, s); $^{31}$P NMR (121.5 MHz, CDCl$_3$) d 157.1 (1P, s).

Example 24

Oxazaphospholidine Monomer 1a

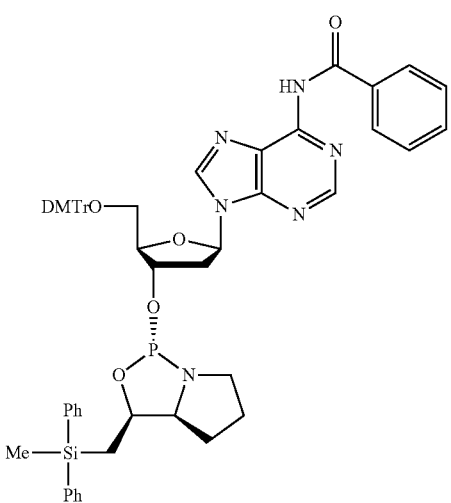

Compound 1a was obtained by using "5'-O-(DMTr)-6-N-(benzoyl)adenosine" instead of "5'-O-(DMTr)-2-N-(phenoxyacetyl)-6-O-(cyanoethyl)guanosine" in a similar manner to compound 3a.

$^1$H NMR (600 MHz, CDCl$_3$) d 8.71 (1H, s), 8.12 (1H, s), 8.04 (2H, d, J=7.8 Hz), 7.62-7.15 (23H, m), 6.80-6.75 (4H, m), 6.37 (1H, dd, J=7.8, 6.0 Hz), 4.94-4.88 (1H, m), 4.80 (1H, ddd, J=12.0, 6.0, 5.4 Hz), 4.07-4.04 (1H, m), 3.76 (6H, s), 3.58-3.49 (1H, m), 3.41-3.34 (1H, m), 3.33 (1H, dd, J=10.8, 4.8 Hz), 3.25 (1H, dd, J=10.8, 4.8 Hz), 3.13-3.06 (1H, m), 2.66-2.58 (1H, m), 2.40-2.35 (1H, m), 1.91-1.84 (1H, m), 1.73-1.66 (1H, m), 1.56 (1H, dd, J=15.0, 9.0 Hz), 1.44 (1H, dd, J=15.0, 5.4 Hz), 1.47-1.41 (1H, m), 1.30-1.23 (1H, m), 0.63 (3H, s); $^{31}$P NMR (243.0 MHz, CDCl$_3$) d 151.8 (1P, s).

Example 25

Oxazaphospholidine Monomer 1b

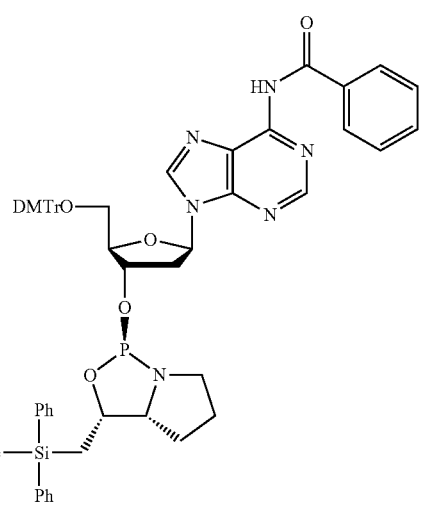

Compound 1b was obtained by using III-b instead of III-a in a similar manner to compound 1a.

$^1$H NMR (300 MHz, CDCl$_3$) d 9.06 (1H, brs), 8.76 (1H, s), 8.12 (1H, s), 8.07-7.99 (2H, m), 7.64-7.14 (22H, m), 6.83-6.75 (4H, m), 6.25 (1H, t, J=6.6 Hz), 4.86-4.75 (2H, m), 4.20-4.15 (1H, m), 3.77 (6H, s), 3.61-3.38 (2H, m), 3.36 (1H, dd, J=10.2, 4.2 Hz), 3.27 (1H, dd, J=10.2, 4.2 Hz), 3.27-3.13 (1H, m), 2.71-2.59 (1H, m), 2.12-2.01 (1H, m), 1.94-1.42 (5H, m), 1.36-1.20 (1H, m), 0.67 (3H, s); $^{31}$P NMR (121.5 MHz, CDCl$_3$) d 157.3 (1P, s).

Example 26

Oxazaphospholidine Monomer 2a

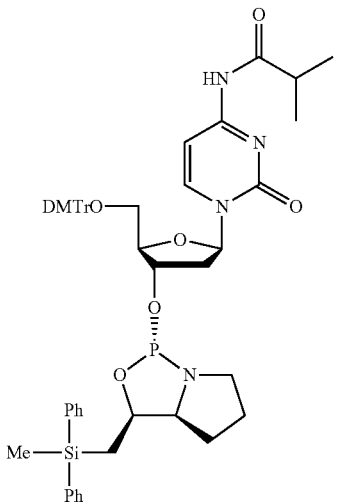

Compound 2a was obtained by using "5'-O-(DMTr)-4-N-(isobutyryl)cytidine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 8.33 (1H, brs), 8.17 (1H, d, J=7.5 Hz), 7.52-7.22 (19H, m), 7.07 (1H, d, J=7.5 Hz), 6.88-6.81 (4H, m), 6.20 (1H, t, J=6.2 Hz), 4.81-4.64 (2H, m), 3.93-3.87 (1H, m), 3.79 (6H, s), 3.59-3.43 (1H, m), 3.39-3.29 (3H, m), 3.16-3.02 (1H, m), 2.69-2.52 (2H, m), 2.12-2.00 (1H, m), 1.91-1.50 (3H, m), 1.47-1.32 (2H, m), 1.27-1.16 (7H, m), 0.60 (3H, s); $^{31}$P NMR (121.5 MHz, CDCl$_3$) d 154.8 (1P, s).

Example 27

Oxazaphospholidine Monomer 2b

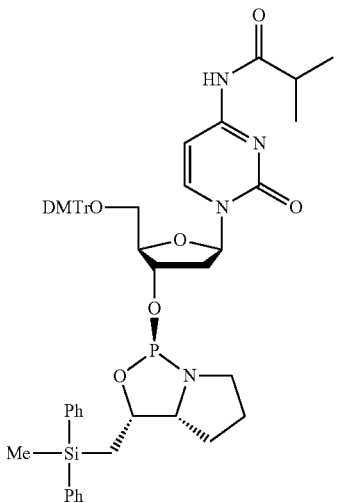

Compound 2b was obtained by using III-b instead of III-a in a similar manner to compound 2a.

$^1$H NMR (300 MHz, CDCl$_3$) d 8.33 (1H, d, J=7.5 Hz), 8.23 (1H, brs), 7.57-7.22 (19H, m), 7.12 (1H, d, J=7.5 Hz), 6.88-6.81 (4H, m), 6.15 (1H, dd, J=6.6, 4.2 Hz), 4.82-4.63 (2H, in), 4.03-3.97 (1H, in), 3.80 (6H, s), 3.55-3.26 (4H, in), 3.19-3.05 (1H, in), 2.59 (1H, quintet, J=6.9 Hz), 2.39-2.27 (1H, m), 2.21-2.10 (1H, m), 1.90-1.56 (3H, m), 1.50-1.32 (2H, m), 1.26-1.17 (7H, m), 0.66 (3H, s); $^{31}$P NMR (121.5 MHz, CDCl$_3$) d 157.2 (1P, s).

Example 28

Oxazaphospholidine Monomer 4a

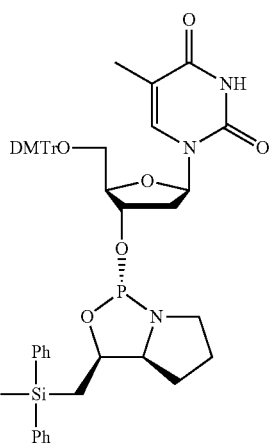

Compound 4a was obtained by using "5'-O-(DMTr)thymidine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 7.58-7.23 (21H, m), 6.86-6.79 (4H, m), 6.35 (1H, dd, J=8.1, 5.7 Hz), 4.79-4.67 (2H, m), 3.83-3.78 (1H, m), 3.78 (6H, s), 3.59-3.43 (1H, m), 3.34 (1H, dd, J=10.5, 2.4 Hz), 3.35-3.24 (1H, m), 3.20 (1H, dd, J=10.5, 2.4 Hz), 3.16-3.02 (1H, m), 2.36-2.26 (1H, m), 2.15-2.02 (1H, m), 1.92-1.77 (1H, m), 1.74-1.59 (1H, m), 1.52 (1H, dd, J=14.7, 9.0 Hz), 1.40 (3H, s), 1.45-1.15 (3H, m), 0.60 (3H, s); $^{31}$P NMR (121.5 MHz, CDCl$_3$) d 153.7 (1P, s).

Example 29

Oxazaphospholidine Monomer 4b

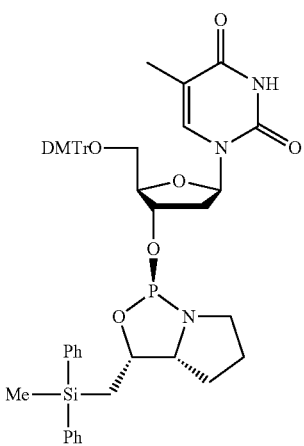

4b

Compound 4b was obtained by using III-b instead of III-a in a similar manner to compound 4a.

$^1$H NMR (300 MHz, CDCl$_3$) d 8.46 (1H, brs), 7.59-7.20 (20H, m), 6.86-6.79 (4H, m), 6.26 (1H, t, J=6.8 Hz), 4.78-4.65 (2H, m), 4.01-3.95 (1H, m), 3.78 (6H, s), 3.55-3.40 (1H, m), 3.42 (1H, dd, J=10.5, 2.7 Hz), 3.40-3.28 (1H, m), 3.22 (1H, dd, J=10.5, 3.0 Hz), 3.19-3.06 (1H, m), 2.16-1.95 (2H, m), 1.90-1.54 (3H, m), 1.49-1.35 (1H, m), 1.43 (3H, s), 1.34-1.17 (2H, m), 0.67 (3H, s); $^{31}$P NMR (121.5 MHz, CDCl$_3$) d 156.2 (1P, s).

Example 30

Oxazaphospholidine Monomer 5a

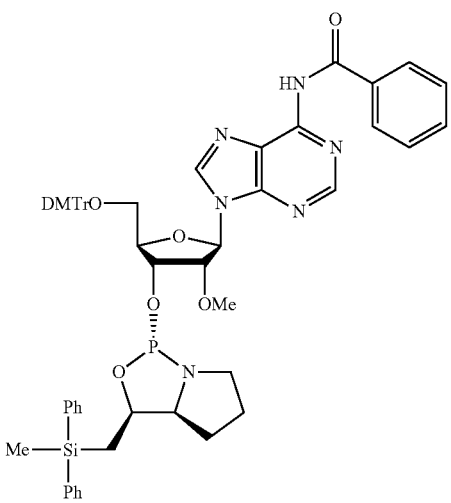

5a

Compound 5a was obtained by using "5'-O-(DMTr)-2'-O-methyl-6-N-(benzoyl)adenosine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 8.66 (1H, s), 8.13 (1H, s), 8.03 (2H, d, J=7.2 Hz), 7.64-7.16 (23H, m), 6.79 (4H, d, J=8.7 Hz), 6.08 (1H, d, J=6.3 Hz), 4.91-4.81 (1H, m), 4.77-4.69 (1H, m), 4.64-4.57 (1H, m), 4.15-4.10 (1H, in), 3.76 (6H, s), 3.60-3.23 (4H, m), 3.35 (3H, s), 3.14-3.00 (1H, m), 1.90-1.19 (6H, m), 0.62 (3H, s); $^{31}$P NMR (121.5 MHz, CDCl$_3$) d 155.8 (1P, s).

Example 31

Oxazaphospholidine Monomer 5b

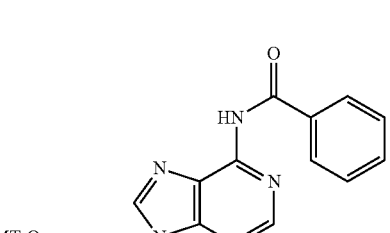

5b

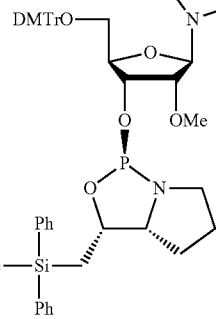

Compound 5b was obtained by using III-b instead of III-a in a similar manner to compound 5a.

$^1$H NMR (300 MHz, CDCl$_3$) d 9.12 (1H, brs), 8.73 (1H, s), 8.24 (1H, s), 8.07-8.01 (2H, m), 7.62-7.17 (22H, m), 6.83-6.77 (4H, m), 6.12 (1H, d, J=4.8 Hz), 4.84-4.73 (2H, m), 4.43 (1H, t, J=4.8 Hz), 4.25-4.19 (1H, m), 3.77 (6H, s), 3.55-3.20 (4H, m), 3.28 (3H, s), 3.16-3.03 (1H, m), 1.90-1.17 (6H, m), 0.65 (3H, s); $^{31}$P NMR (121.5 MHz, CDCl$_3$) d 155.0 (1P, s).

Example 32

Oxazaphospholidine Monomer 6a

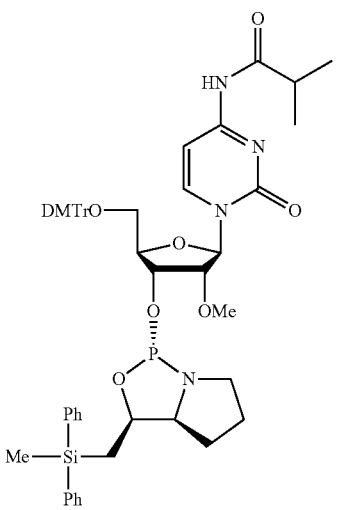

6a

Compound 6a was obtained by using "5'-O-(DMTr)-2'-O-methyl-4-N-(isobutyryl)cytidine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 8.49 (1H, d, J=7.2 Hz), 7.58-7.20 (19H, m), 6.96 (1H, d, J=7.2 Hz), 6.90-6.82 (4H, m), 5.98 (1H, s), 4.84 (1H, dd, J=13.1, 7.5 Hz), 4.59 (1H, dt, J=8.3, 4.5 Hz), 4.19-4.13 (1H, m), 3.79 (6H, s), 3.78-3.72 (1H, m), 3.63-3.40 (3H, m), 3.55 (3H, s), 3.36-3.24 (1H, m), 3.09-2.95 (1H, m), 2.59 (1H, septet, J=6.9 Hz), 1.85-1.53 (5H, m), 1.48-1.37 (1H, m), 1.24-1.17 (6H, m), 0.59 (3H, s); $^{31}$P NMR (121.5 MHz, CDCl$_3$) d 155.2 (1P, s).

Example 33

Oxazaphospholidine Monomer 6b

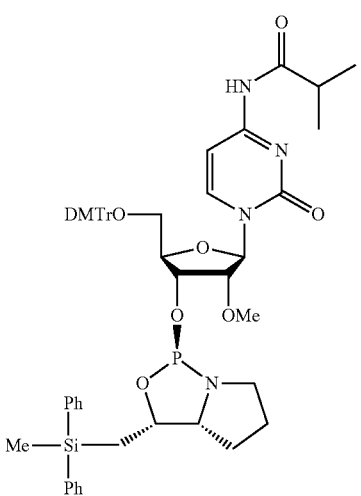

6b

Compound 6b was obtained by using III-b instead of III-a in a similar manner to compound 6a.

$^1$H NMR (300 MHz, CDCl$_3$) d 8.62 (1H, d, J=7.5 Hz), 7.57-7.23 (19H, m), 7.02 (1H, d, J=7.5 Hz), 6.89-6.81 (4H, m), 5.92 (1H, s), 4.90 (1H, dt, J=9.0, 5.7 Hz), 4.61 (1H, dt, J=8.7, 4.8 Hz), 4.25-4.17 (1H, m), 3.81 (6H, s), 3.67 (1H, d, J=4.5 Hz), 3.62-3.25 (4H, m), 3.38 (3H, s), 3.16-3.02 (1H, m), 2.58 (1H, septet, J=6.9 Hz), 1.87-1.40 (6H, m), 1.26-1.14 (6H, m), 0.64 (3H, s); $^{31}$P NMR (121.5 MHz, CDCl$_3$) d 158.2 (1P, s).

Example 34

Oxazaphospholidine Monomer 7a

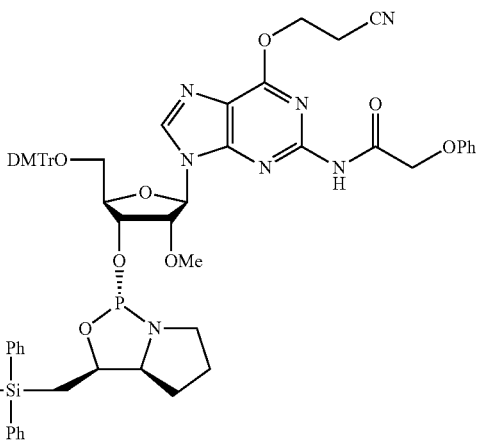

7a

Compound 7a was obtained by using "5'-O-(DMTr)-2'-O-methyl-2-N-(phenoxyacetyl)-6-O-(cyanoethyl)guanosine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 8.67 (1H, brs), 8.01 (1H, s), 7.56-7.16 (24H, m), 6.83-6.74 (4H, m), 6.08 (1H, d, J=6.9 Hz), 4.85-4.76 (1H, m), 4.84 (2H, t, J=6.6 Hz), 4.65-4.56 (1H, m), 4.59 (2H, brs), 4.48 (1H, dd, J=6.6, 5.1 Hz), 4.09-4.05 (1H, m), 3.75 (6H, s), 3.60-3.42 (2H, m), 3.40-3.26 (2H, m), 3.35 (3H, s), 3.18-3.05 (1H, m), 3.08 (2H, t, J=6.6 Hz), 1.89-1.49 (3H, m), 1.48-1.16 (3H, m), 0.59 (3H, s); $^{31}$P NMR (121.5 MHz, CDCl$_3$) d 156.9 (1P, s).

Example 35

Oxazaphospholidine Monomer 7b

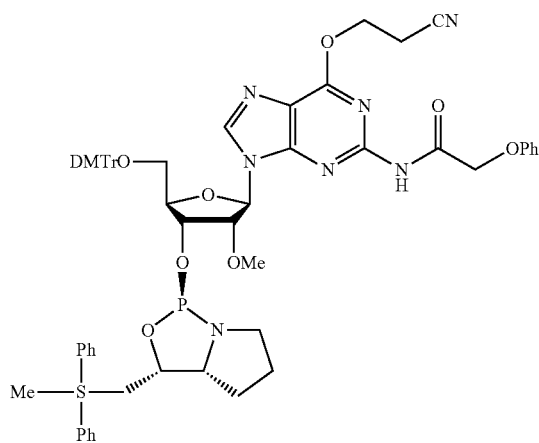

Compound 7b was obtained by using III-b instead of III-a in a similar manner to compound 7a.

$^1$H NMR (300 MHz, CDCl$_3$) d 8.74 (1H, brs), 8.09 (1H, s), 7.56-6.94 (24H, m), 6.84-6.71 (4H, m), 6.09 (1H, d, J=4.8 Hz), 4.83-4.70 (2H, m), 4.83 (2H, t, J=6.6 Hz), 4.63 (2H, brs), 4.35 (1H, t, J=5.0 Hz), 4.23-4.16 (1H, m), 3.75 (6H, s), 3.58-3.19 (4H, m), 3.32 (3H, s), 3.16-3.04 (1H, m), 3.07 (2H, t, J=6.6 Hz), 1.90-1.55 (3H, m), 1.48-1.15 (3H, m), 0.64 (3H, s); $^{31}$P NMR (121.5 MHz, CDCl$_3$) d 154.6 (1P, s).

Example 36

Oxazaphospholidine Monomer 8a

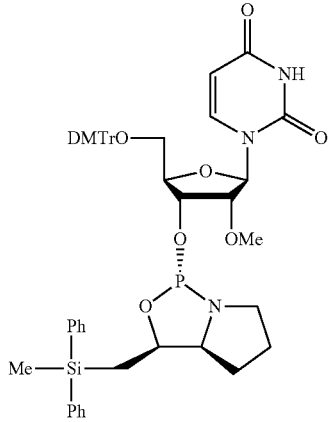

Compound 8a was obtained by using "5'-O-(DMTr)-2'-O-(methyl)uridine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 7.91 (1H, d, J=7.8 Hz), 7.58-7.20 (19H, m), 6.88-6.80 (4H, m), 5.96 (1H, d, J=3.3 Hz), 5.19 (1H, d, J=7.8 Hz), 4.88-4.78 (1H, m), 4.66-4.57 (1H, m), 4.03-3.95 (1H, m), 3.90-3.74 (1H, m), 3.78 (6H, s), 3.77-3.71 (1H, m), 3.58-3.29 (2H, m), 3.45 (3H, s), 3.13-2.82 (2H, m), 1.88-1.53 (3H, m), 1.49-1.16 (3H, m), 0.60 (3H, s); $^{31}$P NMR (121.5 MHz, CDCl$_3$) d 155.3 (1P, s).

Example 37

Oxazaphospholidine Monomer 8b

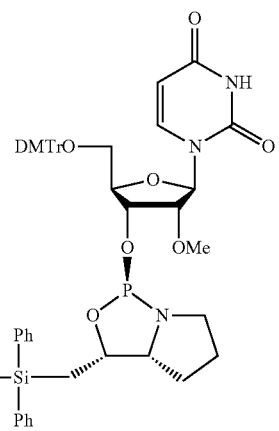

Compound 8b was obtained by using III-b instead of III-a in a similar manner to compound 8a.

$^1$H NMR (300 MHz, CDCl$_3$) d 8.10 (1H, d, J=8.4 Hz), 7.58-7.20 (19H, m), 6.87-6.79 (4H, m), 5.89 (1H, d, J=1.5 Hz), 5.21 (1H, d, J=8.4 Hz), 4.92-4.82 (1H, m), 4.73-4.63 (1H, m), 4.15-4.08 (1H, m), 3.89-3.73 (1H, m), 3.78 (6H, s), 3.66-3.62 (1H, m), 3.57-3.27 (2H, m), 3.30 (3H, s), 3.17-2.82 (2H, m), 1.89-1.55 (3H, m), 1.55-1.40 (1H, m), 1.35-1.15 (2H, m), 0.66 (3H, s); $^{31}$P NMR (121.5 MHz, CDCl$_3$) d 157.5 (1P, s).

Example 38

Oxazaphospholidine Monomer 9a

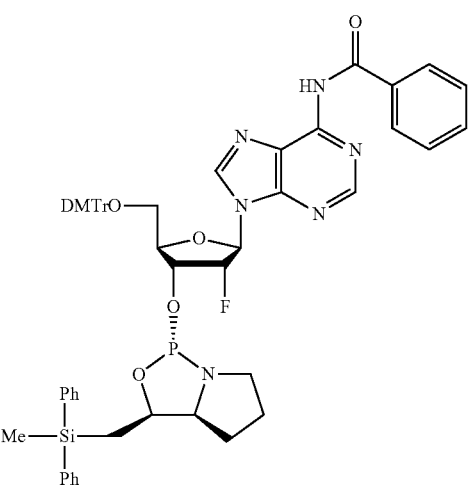

Compound 9a was obtained by using "5'-O-(DMTr)-2'-deoxy-2'-fluoro-6-N-(benzoyl)adenosine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 8.64 (1H, s), 8.14 (1H, s), 8.06-8.01 (2H, m), 7.63-7.07 (23H, m), 6.78-6.70 (4H, m), 6.12 (1H, dd, J=18.0, 2.4 Hz), 5.24-5.01 (2H, m), 4.94-4.84 (1H, m), 4.17-4.06 (1H, m), 3.73 (6H, s), 3.55-3.40 (3H, m), 3.30-3.22 (1H, m), 3.03-2.88 (1H, m), 1.92-1.19 (6H, m), 0.62 (3H, s); $^{31}$P NMR (121.5 MHz, CDCl$_3$) d 150.5 (1P, d, J=7.7 Hz).

Example 39

Oxazaphospholidine Monomer 9b

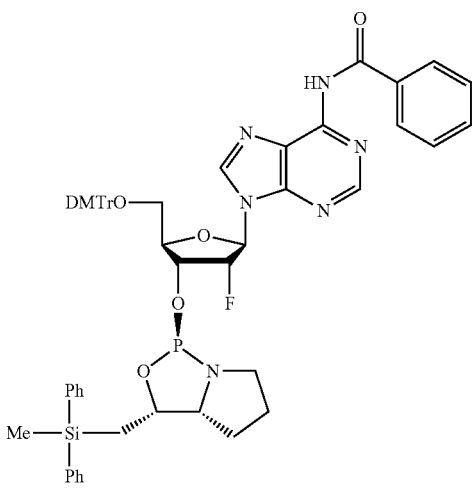

9b

Compound 9b was obtained by using III-b instead of III-a in a similar manner to compound 9a.

$^1$H NMR (300 MHz, CDCl$_3$) d 9.07 (1H, brs), 8.80 (1H, s), 8.24 (1H, s), 8.08-8.01 (2H, m), 7.66-7.15 (22H, m), 6.81-6.75 (4H, m), 6.14 (1H, dd, J=18.0, 1.8 Hz), 5.16-4.91 (3H, m), 4.28-4.21 (1H, m), 3.76 (6H, s), 3.57-3.11 (5H, m), 1.82-1.16 (6H, m), 0.65 (3H, s); $^{31}$P NMR (121.5 MHz, CDCl$_3$) d 157.8 (1P, d, J=5.6 Hz).

Example 40

Oxazaphospholidine Monomer 10a

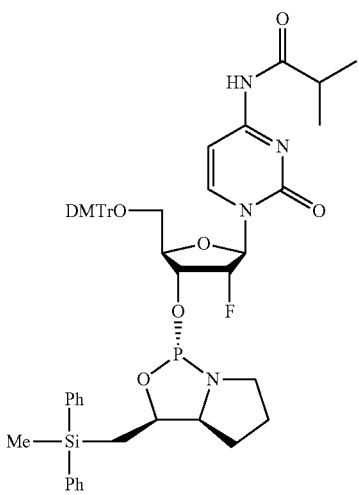

10a

Compound 10a was obtained by using "5'-O-(DMTr)-2'-deoxy-2'-fluoro-4-N-(isobutyryl)cytidine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 8.66 (1H, brs), 8.41 (1H, d, J=7.5 Hz), 7.55-7.20 (19H, m), 7.01 (1H, d, J=7.5 Hz), 6.89-6.81 (4H, m), 6.06 (1H, d, J=15.9 Hz), 4.85 (1H, dd, J=51.4, 3.9 Hz), 4.84 (1H, dd, J=12.9, 7.5 Hz), 4.77-4.59 (1H, m), 4.15-4.08 (1H, m), 3.79 (6H, s), 3.63-3.29 (4H, m), 3.10-2.96 (1H, m), 2.65 (1H, septet, J=6.9 Hz), 1.85-1.53 (3H, m), 1.48-1.17 (3H, m), 1.21 (3H, d, J=4.8 Hz), 1.19 (3H, d, J=4.8 Hz), 0.59 (3H, s); $^{31}$P NMR (121.5 MHz, CDCl$_3$) d 155.5 (1P, d, J=6.6 Hz).

Example 41

Oxazaphospholidine Monomer 10b

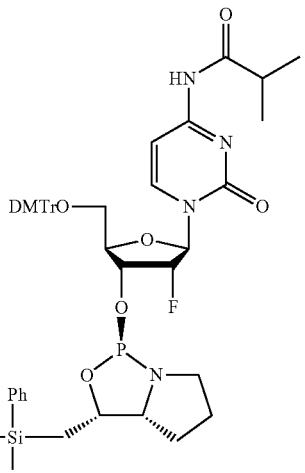

10b

Compound 10b was obtained by using III-b instead of III-a in a similar manner to compound 10a.

$^1$H NMR (300 MHz, CDCl$_3$) d 8.53 (1H, d, J=7.5 Hz), 7.57-7.23 (20H, m), 7.10 (1H, d, J=7.5 Hz), 6.89-6.81 (4H, m), 6.10 (1H, d, J=15.9 Hz), 5.00-4.92 (1H, m), 4.84 (1H, dd, J=51.5, 3.3 Hz), 4.75-4.58 (1H, m), 4.24 (1H, d, J=9.3 Hz), 3.81 (6H, s), 3.65-3.39 (3H, m), 3.32-3.06 (2H, m), 2.59 (1H, septet, J=6.9 Hz), 1.88-1.53 (4H, m), 1.49-1.34 (2H, m), 1.27-1.18 (6H, m), 0.65 (3H, s); $^{31}$P NMR (121.5 MHz, CDCl$_3$) d 159.0 (1P, d, J=4.4).

Example 42

Oxazaphospholidine Monomer 11a

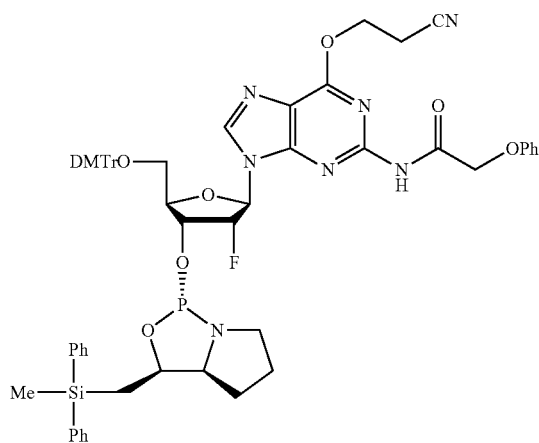

Compound 11a was obtained by using "5'-O-(DMTr)-2'-deoxy-2'-fluoro-2-N-(phenoxyacetyl)-6-O-(cyanoethyl)guanosine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 8.74 (1H, brs), 8.03 (1H, s), 7.55-6.94 (24H, m), 6.80-6.69 (4H, m), 6.21 (1H, dd, J=14.9, 3.6 Hz), 5.34 (1H, dt, J=52.3, 3.6 Hz), 5.01-4.75 (2H, m), 4.84 (1H, t, J=6.6 Hz), 4.62 (2H, brs), 4.15-4.07 (1H, m), 3.73 (6H, s), 3.59-3.29 (4H, m), 3.15-3.00 (1H, m), 3.07 (2H, t, J=6.6 Hz), 1.90-1.49 (3H, m), 1.47-1.12 (3H, m), 0.58 (3H, s); $^{31}$P NMR (121.5 MHz, CDCl$_3$) d 155.6 (1P, d, J=10.9 Hz).

Example 43

Oxazaphospholidine Monomer 11b

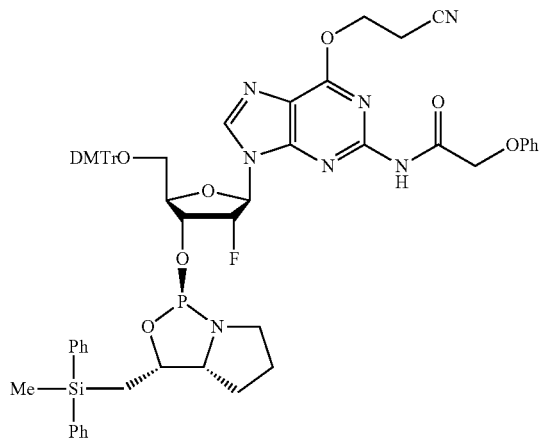

Compound 11b was obtained by using III-b instead of III-a in a similar manner to compound 11a.

$^1$H NMR (300 MHz, CDCl$_3$) d 8.81 (1H, brs), 8.06 (1H, s), 7.55-6.95 (24H, m), 6.77-6.69 (4H, m), 6.06 (1H, d, J=17.1 Hz), 5.24-5.08 (1H, m), 5.04-4.80 (2H, m), 4.87 (1H, t, J=6.6 Hz), 4.62 (2H, brs), 4.25-4.19 (1H, m), 3.73 (6H, s), 3.58-3.02 (5H, m), 3.10 (2H, t, J=6.6 Hz), 1.90-1.56 (3H, m), 1.50-1.15 (3H, m), 0.63 (3H, s); $^{31}$P NMR (121.5 MHz, CDCl$_3$) d 158.0 (1P, d, J=4.4 Hz).

Example 44

Oxazaphospholidine Monomer 12a

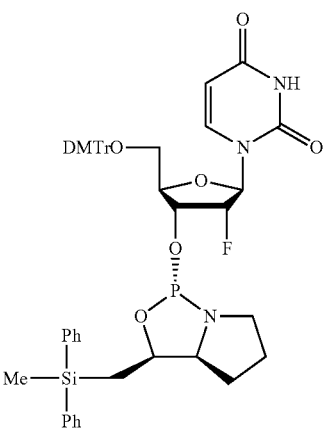

Compound 12a was obtained by using "5'-O-(DMTr)-2'-deoxy-2'-fluorouridine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 7.85 (1H, d, J=8.1 Hz), 7.58-7.20 (19H, m), 6.87-6.79 (4H, m), 5.98 (1H, d, J=16.5 Hz), 5.23 (1H, d, J=8.1 Hz), 4.86-4.61 (3H, m), 3.99 (1H, d, J=6.9 Hz), 3.76 (6H, d, J=3.0 Hz), 3.56-3.34 (4H, m), 3.10-2.96 (1H, m), 1.88-1.74 (1H, m), 1.72-1.52 (2H, m), 1.48-1.16 (3H, m), 0.61 (3H, s); $^{31}$P NMR (121.5 MHz, CDCl$_3$) d 154.3 (1P, d, J=8.9 Hz).

Example 45

Oxazaphospholidine Monomer 12b

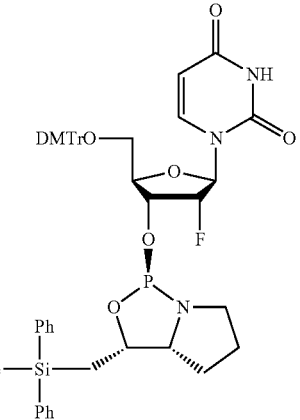

Compound 12b was obtained by using III-b instead of III-a in a similar manner to compound 12a.

$^1$H NMR (300 MHz, CDCl$_3$) d 8.01 (1H, d, J=8.4 Hz), 7.58-7.20 (19H, m), 6.87-6.79 (4H, m), 6.03 (1H, d, J=16.2 Hz), 5.29 (1H, d, J=8.4 Hz), 4.96 (1H, dd, J=13.1, 7.5 Hz), 4.80-4.54 (2H, m), 4.15 (1H, d, J=9.0 Hz), 3.78 (6H, s), 3.61-3.39 (3H, m), 3.37-3.25 (1H, m), 3.23-3.09 (1H, m), 1.91-1.56 (3H, m), 1.51-1.13 (3H, m), 0.66 (3H, s); $^{31}$P NMR (121.5 MHz, CDCl$_3$) d 158.9 (1P, d, J=4.4 Hz).

Example 46

Oxazaphospholidine Monomer 13a

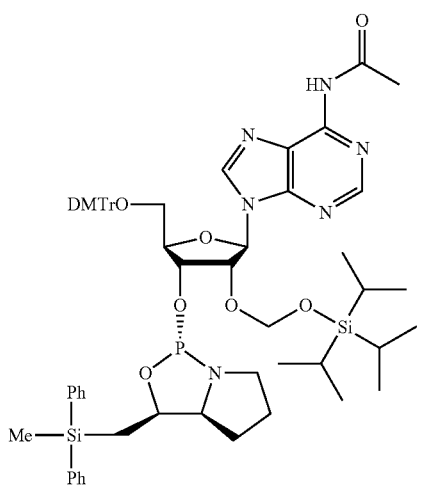

Compound 13a was obtained by using "5'-O-(DMTr)-2'-O-TOM-6-N-(acetyl)adenosine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 8.82 (1H, brs), 8.49 (1H, s), 8.10 (1H, s), 7.58-7.17 (19H, m), 6.83-6.73 (4H, m), 6.11 (1H, d, J=6.6 Hz), 5.15 (1H, dd, J=6.6, 5.4 Hz), 4.98-4.77 (4H, m), 4.18-4.11 (1H, in), 3.76 (6H, s), 3.59-3.25 (4H, in), 3.16-3.02 (1H, m), 2.62 (3H, s), 1.91-1.53 (3H, m), 1.49-1.18 (3H, m), 0.96-0.80 (3H, m), 0.90 (18H, s), 0.62 (3H, s); $^{31}$P NMR (121.5 MHz, CDCl$_3$) d 156.7 (1P, s).

Example 47

Oxazaphospholidine Monomer 13b

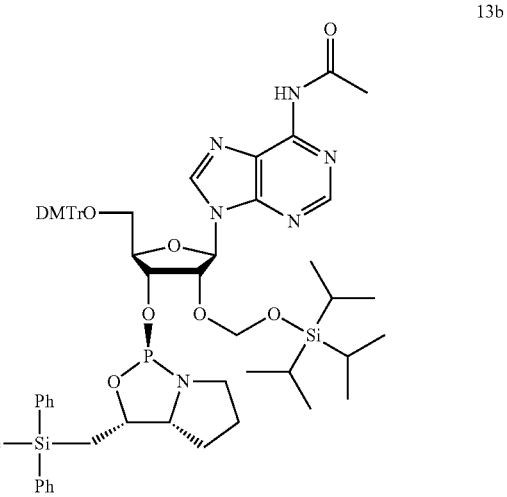

Compound 13b was obtained by using III-b instead of III-a in a similar manner to compound 13a.

$^1$H NMR (300 MHz, CDCl$_3$) d 8.56 (1H, brs), 8.55 (1H, s), 8.13 (1H, s), 7.57-7.17 (19H, m), 6.82-6.73 (4H, m), 6.16 (1H, d, J=5.7 Hz), 5.06 (1H, t, J=5.6 Hz), 4.93 (1H, d, J=5.1 Hz), 4.83 (1H, d, J=5.1 Hz), 4.81-4.69 (2H, m), 4.27-4.19 (1H, m), 3.76 (6H, s), 3.55-3.40 (2H, in), 3.33-3.16 (2H, in), 3.12-2.97 (1H, in), 2.63 (3H, s), 1.88-1.52 (3H, m), 1.45-1.16 (3H, m), 0.91-0.79 (3H, m), 0.86 (18H, s), 0.64 (3H, s); $^{31}$P NMR (121.5 MHz, CDCl$_3$) d 154.8 (1P, s).

Example 48

Oxazaphospholidine Monomer 14a

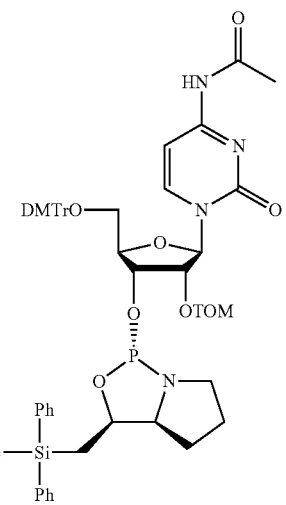

Compound 14a was obtained by using "5'-O-(DMTr)-2'-O-TOM-4-N-(acetyl)cytidine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 10.04 (1H, brs), 8.30 (1H, d, J=7.5 Hz), 7.51-7.21 (19H, m), 6.99 (1H, d, J=7.5 Hz), 6.89-6.81 (4H, m), 6.12 (1H, d, J=3.3 Hz), 5.07 (1H, d, J=4.8 Hz), 5.05 (1H, d, J=4.8 Hz), 4.84-4.75 (1H, m), 4.62-4.52 (1H, m), 4.31-4.25 (1H, m), 4.08-4.01 (1H, m), 3.78 (6H, d, J=3.0 Hz), 3.55-3.23 (4H, m), 3.10-2.96 (1H, m), 2.24 (3H, s), 1.84-1.49 (3H, m), 1.46-0.96 (24H, m), 0.58 (3H, s); $^{31}$P NMR (121.5 MHz, CDCl$_3$) d 156.5 (1P, s).

Example 49

Oxazaphospholidine Monomer 14b

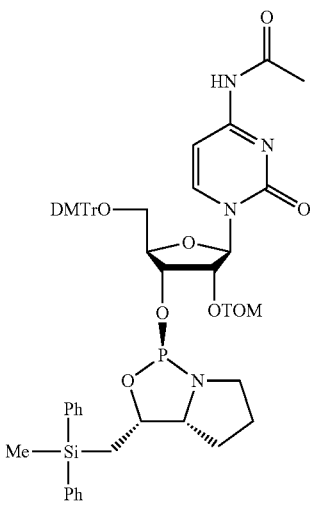

Compound 14b was obtained by using III-b instead of III-a in a similar manner to compound 14a.

$^1$H NMR (300 MHz, CDCl$_3$) d 10.19 (1H, brs), 8.46 (1H, d, J=7.5 Hz), 7.54-7.23 (19H, m), 7.01 (1H, d, J=7.5 Hz), 6.88-6.79 (4H, m), 6.19 (1H, d, J=1.8 Hz), 5.11 (1H, d, J=4.8 Hz), 5.07 (1H, d, J=4.8 Hz), 4.81-4.71 (1H, m), 4.60-4.51 (1H, m), 4.26-4.18 (2H, m), 3.79 (6H, s), 3.63-3.55 (1H, m), 3.48-3.28 (2H, m), 3.21-2.94 (2H, m), 2.26 (3H, s), 1.81-1.49 (3H, m), 1.43-0.96 (24H, m), 0.62 (3H, s); $^{31}$P NMR (121.5 MHz, CDCl$_3$) d 156.4 (1P, s).

Example 50

Oxazaphospholidine Monomer 15a

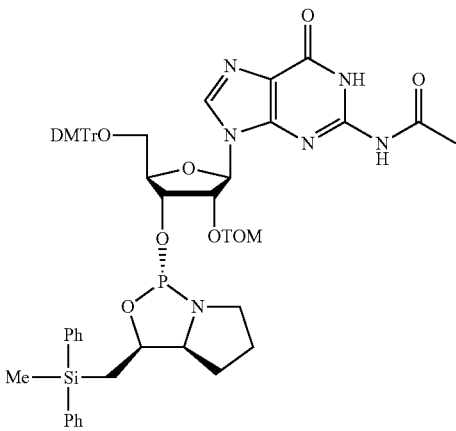

Compound 15a was obtained by using "5'-O-(DMTr)-2'-O-TOM-2-N-(acetyl)guanosine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 7.70 (1H, s), 7.63-7.13 (21H, m), 6.84-6.76 (4H, m), 5.77 (1H, d, J=8.4 Hz), 5.41-5.33 (1H, m), 4.90 (2H, s), 4.78-4.68 (2H, m), 3.86 (1H, brs), 3.75 (3H, s), 3.74 (3H, s), 3.56-3.41 (2H, m), 3.32-2.90 (3H, m), 1.92-1.10 (9H, m), 0.97-0.87 (21H, m), 0.52 (3H, s); $^{31}$P NMR (121.5 MHz, CDCl$_3$) d 158.1 (1P, s).

Example 51

Oxazaphospholidine Monomer 15b

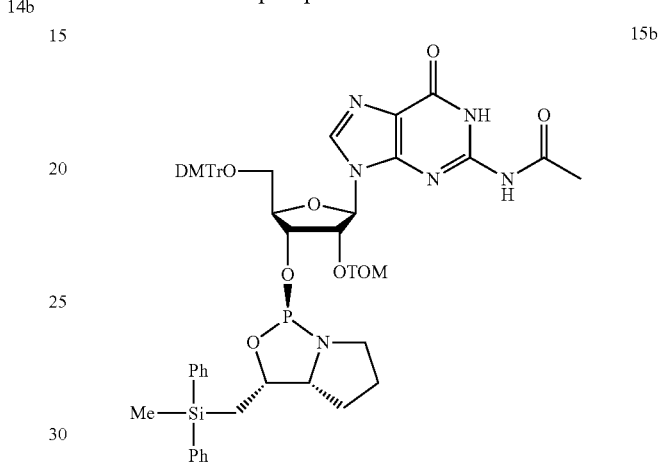

Compound 15b was obtained by using III-b instead of III-a in a similar manner to compound 15a.

$^1$H NMR (300 MHz, CDCl$_3$) d 7.77 (1H, s), 7.56-7.15 (21H, m), 6.82-6.75 (4H, m), 5.86 (1H, d, J=7.5 Hz), 5.26-5.17 (1H, m), 4.95 (1H, d, J=5.4 Hz), 4.85 (1H, d, J=5.4 Hz), 4.78-4.71 (1H, m), 4.59-4.49 (1H, m), 4.10-4.05 (1H, m), 3.74 (6H, s), 3.52-3.37 (2H, m), 3.30-3.18 (1H, m), 3.11-2.85 (2H, m), 1.85-1.15 (9H, m), 0.93-0.84 (21H, m), 0.62 (3H, s); $^{31}$P NMR (121.5 MHz, CDCl$_3$) d 152.3 (1P, s).

Example 52

Oxazaphospholidine Monomer 16a

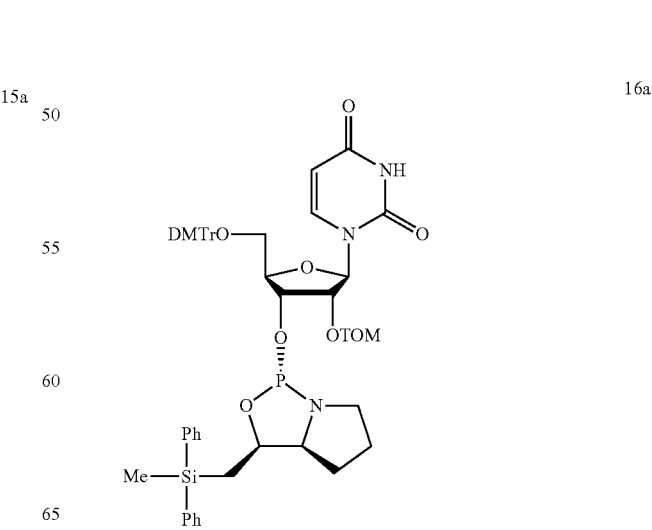

Compound 16a was obtained by using "5'-O-(DMTr)-2'-O-TOM-uridine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 7.76 (1H, d, J=8.1 Hz), 7.55-7.18 (20H, m), 6.88-6.80 (4H, m), 6.11 (1H, d, J=6.0 Hz), 5.32 (1H, d, J=8.1 Hz), 4.99 (1H, d, J=5.1 Hz), 4.93 (1H, d, J=5.1 Hz), 4.84-4.75 (1H, m), 4.54-4.46 (1H, m), 4.38 (1H, t, J=5.7 Hz), 3.87-3.83 (1H, m), 3.78 (3H, s), 3.77 (3H, s), 3.56-3.42 (1H, m), 3.39-3.28 (1H, m), 3.36 (1H, dd, J=11.0, 2.7 Hz), 3.25 (1H, dd, J=11.0, 2.7 Hz), 3.16-3.03 (1H, m), 1.88-1.12 (6H, m), 1.08-0.97 (21H, m), 0.59 (3H, s); $^{31}$P NMR (121.5 MHz, CDCl$_3$) d 156.6 (1P, s).

Example 53

Oxazaphospholidine Monomer 16b

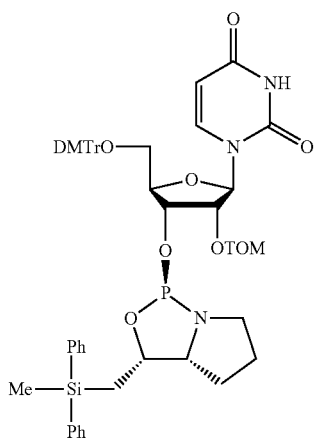

16b

Compound 16b was obtained by using III-b instead of III-a in a similar manner to compound 16a.

$^1$H NMR (600 MHz, CDCl$_3$) d 7.87 (1H, d, J=7.8 Hz), 7.52-7.48 (4H, m), 7.38-7.21 (16H, m), 6.83-6.79 (4H, m), 6.14 (1H, d, J=4.8 Hz), 5.33 (1H, d, J=7.8 Hz), 4.99 (1H, d, J=5.4 Hz), 4.89 (1H, d, J=5.4 Hz), 4.67 (1H, dd, J=13.8, 7.2 Hz), 4.52 (1H, dt, J=10.4, 4.8 Hz), 4.31 (1H, t, J=4.8 Hz), 4.06-4.03 (1H, m), 3.78 (3H, s), 3.77 (3H, s), 3.47 (1H, dd, J=10.4, 2.4 Hz), 3.47-3.39 (1H, m), 3.22-3.17 (2H, m), 3.00 (1H, ddd, J=19.5, 10.4, 4.8 Hz), 1.82-1.74 (1H, m), 1.68-1.58 (1H, m), 1.56 (1H, dd, J=14.4, 8.4 Hz), 1.38 (1H, dd, J=14.4, 7.2 Hz), 1.31-1.25 (1H, m), 1.26-1.17 (1H, m), 1.08-0.98 (21H, m), 0.63 (3H, s); $^{31}$P NMR (243.0 MHz, CDCl$_3$) d 154.3 (1P, s).

Example 54

Oxazapholidine Monomer 17a

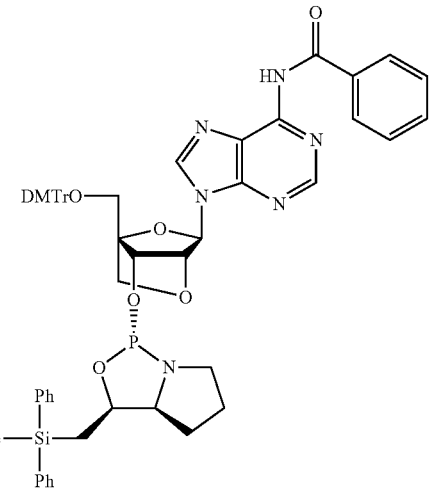

17a

Compound 17a was obtained by using "5'-O-(DMTr)-2'-O,4'-C-methylene-6-N-(benzoyl)adenosine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 9.10 (1H, brs), 8.76 (1H, s), 8.32 (1H, s), 8.04 (2H, d, J=7.2 Hz), 7.64-7.18 (22H, m), 6.84 (4H, d, J=8.7 Hz), 6.10 (1H, s), 4.76 (1H, d J=6.9 Hz), 4.58 (1H, s), 4.61-4.51 (1H, m), 3.91 (1H, d, J=7.8 Hz), 3.77 (1H, d, J=7.8 Hz), 3.75 (6H, s), 3.50 (1H, s), 3.47-3.33 (1H, m), 3.31-3.19 (1H, m), 3.03-2.88 (1H, m), 1.84-1.09 (6H, m), 0.51 (3H, s); $^{31}$P NMR (121.5 MHz, CDCl$_3$) d 152.9 (1P, s).

Example 55

Oxazaphospholidine Monomer 17b

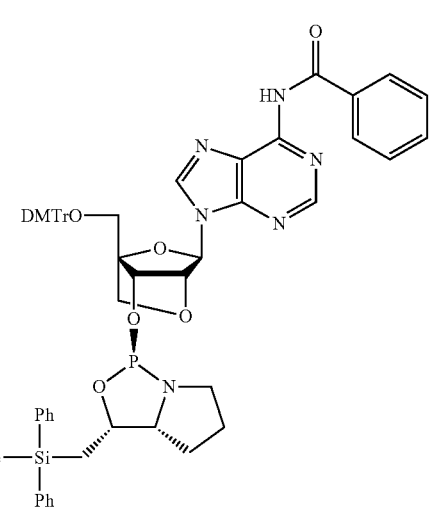

17b

Compound 17b was obtained by using III-b instead of III-a in a similar manner to compound 17a.

$^1$H NMR (300 MHz, CDCl$_3$) d 8.81 (1H, s), 8.30 (1H, s), 8.07-8.00 (2H, m), 7.64-7.17 (22H, m), 6.86-6.79 (4H, m), 6.12 (1H, s), 4.81-4.72 (1H, m), 4.62 (1H, d J=7.2 Hz), 4.57 (1H, s), 3.94 (1H, d, J=7.8 Hz), 3.89 (1H, d, J=7.8 Hz), 3.77 (6H, s), 3.48 (2H, s), 3.46-3.32 (1H, m), 3.24-3.13 (1H, m), 3.10-2.97 (1H, m), 1.84-1.49 (3H, m), 1.42-1.09 (3H, m), 0.58 (3H, s); $^{31}$P NMR (121.5 MHz, CDCl$_3$) d 157.3 (1P, s).

Example 56

Oxazaphospholidine Monomer 18a

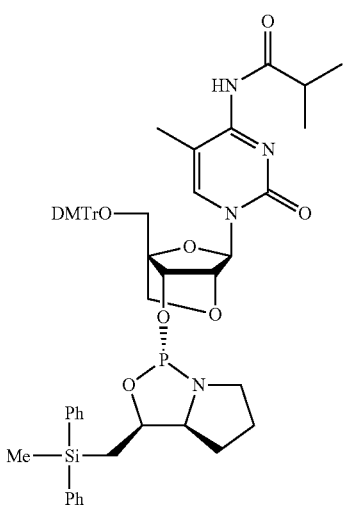

18a

Compound 18a was obtained by using "5'-O-(DMTr)-2'-O,4'-C-methylene-4-N-(isobutyryl)-5-methylcytidine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 7.88 (1H, brs), 7.58-7.18 (20H, m), 6.88-6.80 (4H, m), 5.65 (1H, s), 4.69-4.60 (1H, m), 4.52 (1H, d, J=6.6 Hz), 4.49 (1H, s), 3.81-3.74 (1H, m), 3.75 (3H, s), 3.73 (3H, s), 3.64 (1H, d, J=8.1 Hz), 3.56 (1H, d, J=11.1 Hz), 3.53 (1H, d, J=8.1 Hz), 3.46 (1H, d, J=11.1 Hz), 3.56-3.40 (1H, m), 3.32-3.20 (1H, m), 3.14-3.00 (1H, m), 1.85-1.12 (6H, m), 1.60 (3H, s), 1.19 (6H, d, J=6.9 Hz), 0.55 (3H, s); $^{31}$P NMR (121.5 MHz, CDCl$_3$) d 155.9 (1P, s).

Example 57

Oxazaphospholidine Monomer 18b

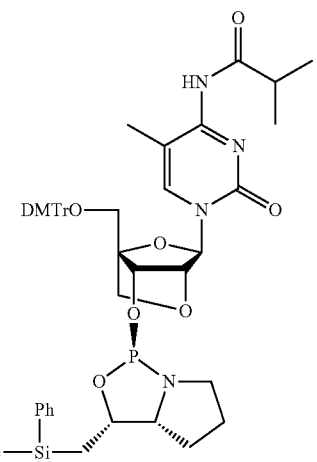

18b

Compound 18b was obtained by using III-b instead of III-a in a similar manner to compound 18a.

$^1$H NMR (300 MHz, CDCl$_3$) d 7.86 (1H, brs), 7.56-7.19 (20H, in), 6.88-6.79 (4H, in), 5.69 (1H, s), 4.86-4.76 (1H, m), 4.46 (1H, s), 4.45 (1H, d, J=7.5 Hz), 3.80-3.75 (1H, m), 3.79 (6H, s), 3.74 (1H, d, J=8.1 Hz), 3.69 (1H, d, J=8.1 Hz), 3.51 (1H, d, J=11.1 Hz), 3.44-3.30 (1H, m), 3.39 (1H, d, J=11.1 Hz), 3.29-3.17 (1H, m), 3.11-2.97 (1H, m), 1.86-1.52 (3H, m), 1.64 (3H, s), 1.45-1.10 (3H, m), 1.21 (6H, d, J=6.6 Hz), 0.62 (3H, s); $^{31}$P NMR (121.5 MHz, CDCl$_3$) d 158.2 (1P, s).

Example 58

Oxazaphospholidine Monomer 19a

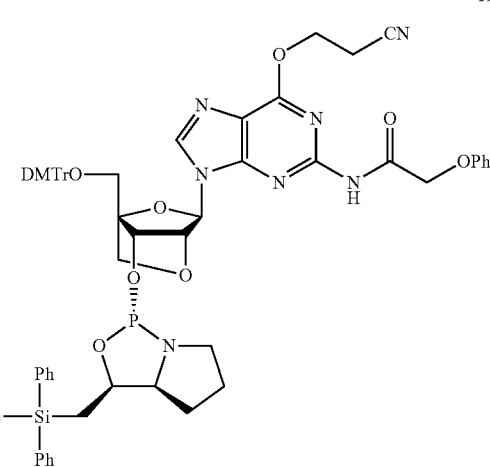

19a

Compound 19a was obtained by using "5'-O-(DMTr)-2'-O,4'-C-methylene-2-N-(phenoxyacetyl)-6-O-(cyanoethyl)

guanosine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 8.71 (1H, brs), 8.16 (1H, s), 7.50-7.17 (21H, m), 7.09-7.01 (3H, m), 6.86-6.79 (4H, in), 6.03 (1H, s), 4.84 (2H, t, J=6.6 Hz), 4.72 (2H, s), 4.68 (1H, d, J=7.2 Hz), 4.55-4.46 (1H, m), 4.50 (1H, s), 3.90 (1H, d, J=7.8 Hz), 3.77 (1H, d, J=7.8 Hz), 3.75 (6H, s), 3.51 (1H, d, J=10.8 Hz), 3.47 (1H, d, J=10.8 Hz), 3.45-3.21 (2H, m), 3.08 (2H, t, J=6.6 Hz), 3.03-2.89 (1H, m), 1.80-1.08 (6H, m), 0.47 (3H, s); $^{31}$P NMR (121.5 MHz, CDCl$_3$) d 153.2 (1P, s).

Example 59

Oxazapholidine Monomer 19b

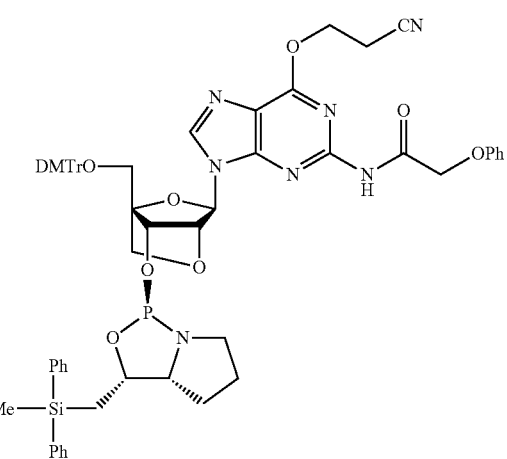

Compound 19b was obtained by using III-b instead of III-a in a similar manner to compound 19a.

$^1$H NMR (300 MHz, CDCl$_3$) d 8.86 (1H, brs), 8.13 (1H, s), 7.55-7.17 (21H, m), 7.08-6.98 (3H, m), 6.95-6.78 (4H, m), 6.01 (1H, s), 4.86 (2H, t, J=6.6 Hz), 4.82-4.73 (1H, m), 4.70 (2H, s), 4.64 (1H, d, J=7.5 Hz), 4.49 (1H, s), 3.94 (1H, d, J=7.8 Hz), 3.89 (1H, d, J=7.8 Hz), 3.77 (6H, s), 3.46 (2H, s), 3.45-3.30 (1H, m), 3.24-3.12 (1H, m), 3.09 (2H, t, J=6.6 Hz), 3.09-2.96 (1H, m), 1.81-1.50 (3H, m), 1.41-1.06 (3H, m), 0.58 (3H, s); $^{31}$P NMR (121.5 MHz, CDCl$_3$) d 157.4 (1P, s).

Example 60

Oxazapholidine Monomer 20a

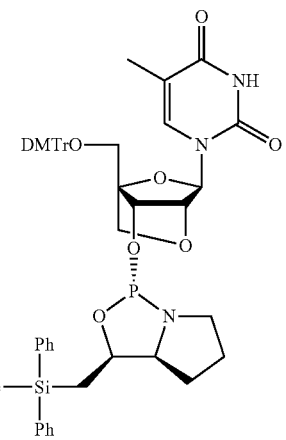

Compound 20a was obtained by using "5'-O-(DMTr)-2'-O,4'-C-methylene-5-methyluridine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 7.71 (1H, d, J=0.9 Hz), 7.50-7.17 (20H, m), 6.87-6.80 (4H, m), 5.61 (1H, s), 4.69-4.60 (1H, m), 4.55 (1H, d, J=6.9 Hz), 4.41 (1H, s), 3.74 (3H, s), 3.73 (3H, s), 3.64 (1H, d, J=7.8 Hz), 3.55 (1H, d, J=7.8 Hz), 3.53 (1H, d, J=10.8 Hz), 3.46 (1H, d, J=10.8 Hz), 3.56-3.42 (1H, m), 3.35-3.24 (1H, m), 3.13-3.00 (1H, m), 1.85-1.45 (3H, m), 1.55 (3H, d, J=0.9 Hz), 1.41-1.12 (3H, m), 0.56 (3H, s); $^{31}$P NMR (121.5 MHz, CDCl$_3$) d 155.1 (1P, s).

Example 61

Oxazapholidine Monomer 20b

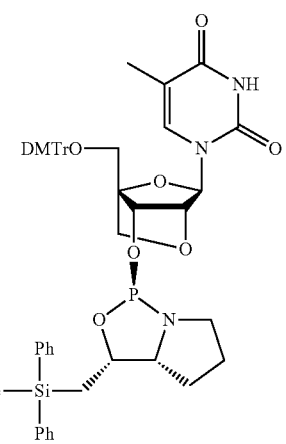

Compound 20b was obtained by using III-b instead of III-a in a similar manner to compound 20a.

$^1$H NMR (300 MHz, CDCl$_3$) d 7.69 (1H, s), 7.56-7.19 (20H, m), 6.88-6.79 (4H, m), 5.66 (1H, s), 4.87-4.77 (1H, m), 4.47 (1H, d, J=7.8 Hz), 4.40 (1H, s), 3.78 (6H, s), 3.74 (1H, d, J=7.8 Hz), 3.68 (1H, d, J=7.8 Hz), 3.50 (1H, d, J=10.8 Hz), 3.46-3.32 (1H, m), 3.39 (1H, d, J=10.8 Hz), 3.30-3.19 (1H, m), 3.12-2.98 (1H, m), 1.85-1.56 (3H, m), 1.59 (3H, s), 1.46-1.12 (3H, m), 0.63 (3H, s); $^{31}$P NMR (121.5 MHz, CDCl$_3$) d 158.1 (1P, s).

Example 62

Oxazaphospholidine Monomer 21a

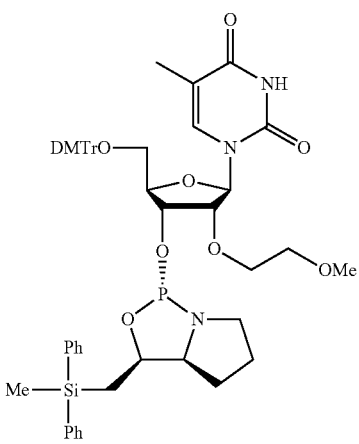

Compound 21a was obtained by using "5'-O-(DMTr)-2'-O-methoxyethyl-5-methyluridine" instead of "5'-O-(DMTr)-2-N-(phenoxyacetyl)-6-O-(cyanoethyl)guanosine" in a similar manner to compound 3a.

$^1$H NMR (300 MHz, CDCl$_3$) d 7.62-7.18 (21H, m), 6.84 (4H, d, J=8.7 Hz), 6.07 (1H, d, J=5.7 Hz), 4.86-4.76 (1H, m), 4.63-4.54 (1H, m), 4.20 (1H, t, J=5.4 Hz), 3.95-3.89 (1H, m), 3.78 (6H, s), 3.78-3.71 (2H, m), 3.60-3.48 (2H, m), 3.44-3.02 (5H, m), 3.31 (3H, s), 1.88-1.15 (6H, m), 1.35 (3H, s), 0.58 (3H, s); $^{31}$P NMR (121.5 MHz, CDCl$_3$) d 156.3 (1P, s).

Example 63

Oxazaphospholidine Monomer 21b

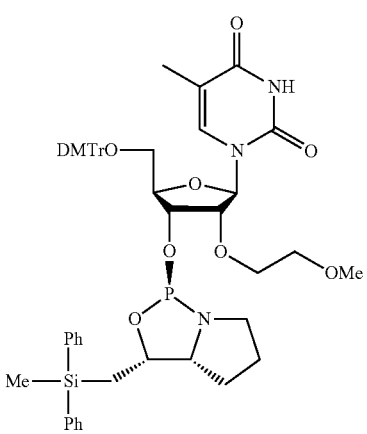

Compound 21b was obtained by using III-b instead of III-a in a similar manner to compound 21a.

$^1$H NMR (300 MHz, CDCl$_3$) d 7.71 (1H, d, J=1.2 Hz), 7.55-7.22 (20H, m), 6.86-6.78 (4H, m), 5.99 (1H, d, J=3.9 Hz), 4.78-4.62 (2H, m), 4.13-4.08 (1H, m), 4.07-4.02 (1H, m), 3.77 (6H, s), 3.77-3.70 (1H, m), 3.65-3.56 (1H, m), 3.52-3.36 (4H, m), 3.33-3.14 (2H, m), 3.29 (3H, s), 3.08-2.94 (1H, m), 1.86-1.72 (1H, m), 1.71-1.55 (2H, m), 1.30 (3H, d, J=1.2 Hz), 1.47-1.16 (3H, m) 0.64 (3H, s); $^{31}$P NMR (121.5 MHz, CDCl$_3$) d 155.6 (1P, s).

Example 64

Oxazaphospholidine Monomer 22a

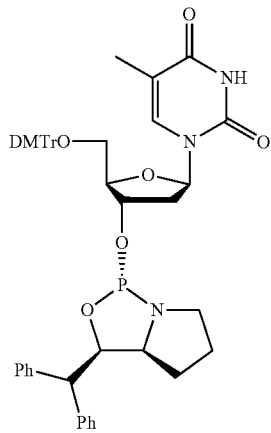

Compound 22a was obtained by using VII-a instead of III-a in a similar manner to compound 4a.

$^1$H NMR (300 MHz, CDCl$_3$) d 7.57 (1H, d, J=0.9 Hz), 7.37-6.94 (20H, m), 6.87-6.78 (4H, m), 6.48 (1H, dd, J=8.6, 5.7 Hz), 5.42 (1H, dd, J=11.0, 5.1 Hz), 4.81-4.71 (1H, m), 4.02 (1H, d, J=11.0 Hz), 3.83 (1H, d, J=2.1 Hz), 3.79 (6H, s), 3.61-3.41 (2H, m), 3.24-3.09 (1H, m), 3.16 (1H, dd, J=10.8, 2.4 Hz), 3.02 (1H, dd, J=10.8, 2.4 Hz), 2.54-2.44 (1H, m), 2.34-2.22 (1H, m), 1.94-1.79 (1H, m), 1.74-1.56 (1H, m), 1.38 (3H, s), 1.38-1.28 (2H, m); $^{31}$P NMR (121.5 MHz, CDCl$_3$) d 160.9 (1P, s).

Example 65

Oxazaphospholidine Monomer 22b

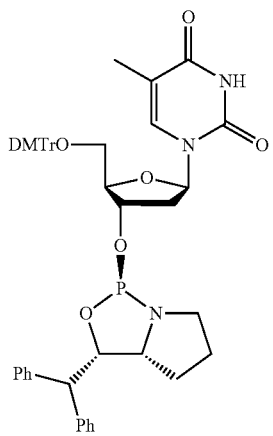

Compound 22b was obtained by using VII-b instead of VII-a in a similar manner to compound 22a.

¹H NMR (300 MHz, CDCl₃) d 7.57 (1H, d, J=1.5 Hz), 7.43-7.11 (20H, m), 6.85-6.78 (4H, m), 6.48 (1H, dd, J=7.5, 5.7 Hz), 5.58 (1H, dd, J=11.4, 5.1 Hz), 4.82-4.73 (1H, m), 4.17-4.02 (2H, m), 3.78 (6H, s), 3.56-3.40 (3H, m), 3.32 (1H, dd, J=10.7, 2.4 Hz), 3.22-3.07 (1H, m), 2.26-2.04 (2H, m), 1.95-1.81 (1H, m), 1.74-1.56 (1H, m), 1.40 (3H, d, J=1.5 Hz), 1.44-1.34 (2H, m); ³¹P NMR (121.5 MHz, CDCl₃) d 162.2 (1P, s).

Example 66

Oxazaphospholidine Monomer 23a

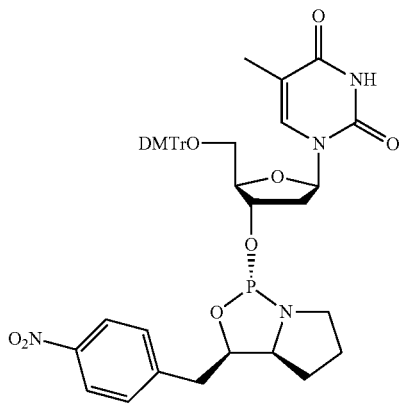

Compound 23a was obtained by using IX-a instead of III-a in a similar manner to compound 4a.

¹H NMR (300 MHz, CDCl₃) d 9.22 (1H, brs), 8.05-7.99 (2H, m), 7.52 (1H, d, J=1.2 Hz), 7.41-7.19 (11H, m), 6.87-6.79 (4H, m), 6.37 (1H, dd, J=8.4, 5.7 Hz), 4.88-4.75 (2H, m), 3.86-3.80 (1H, m), 3.79 (6H, s), 3.64-3.49 (2H, m), 3.27-3.12 (3H, m), 2.97 (2H, d, J=6.6 Hz), 2.51-2.41 (1H, m), 2.33-2.20 (1H, m), 2.03-1.75 (2H, m), 1.72-1.59 (1H, m), 1.46-1.36 (1H, m), 1.40 (3H, s); ³¹P NMR (121.5 MHz, CDCl₃) d 157.5 (1P, s).

Example 67

Oxazaphospholidine Monomer 23b

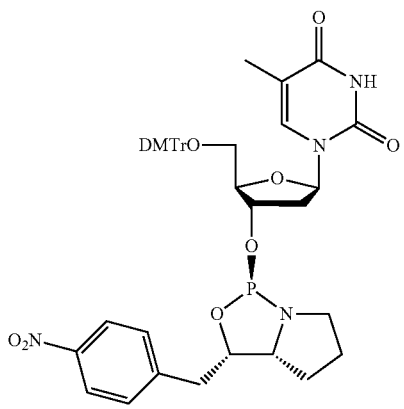

Compound 23b was obtained by using IX-b instead of IX-a in a similar manner to compound 23a.

¹H NMR (300 MHz, CDCl₃) d 8.67 (1H, brs), 8.18-8.11 (2H, m), 7.57 (1H, d, J=1.2 Hz), 7.47-7.22 (11H, m), 6.86-6.79 (4H, m), 6.29 (1H, t, J=6.6 Hz), 4.87 (1H, dt, J=7.5, 5.7 Hz), 4.80-4.72 (1H, m), 4.11-4.05 (1H, m), 3.79 (6H, s), 3.67-3.47 (2H, m), 3.43 (1H, dd, J=10.8, 2.7 Hz), 3.27 (1H, dd, J=10.8, 2.4 Hz), 3.25-3.13 (1H, m), 3.07-2.99 (2H, m), 2.19-2.12 (2H, in), 2.03-1.62 (3H, m), 1.46-1.30 (1H, m), 1.41 (3H, s); ³¹P NMR (121.5 MHz, CDCl₃) d 158.1 (1P, s).

Example 68

Oxazaphospholidine Monomer 24a

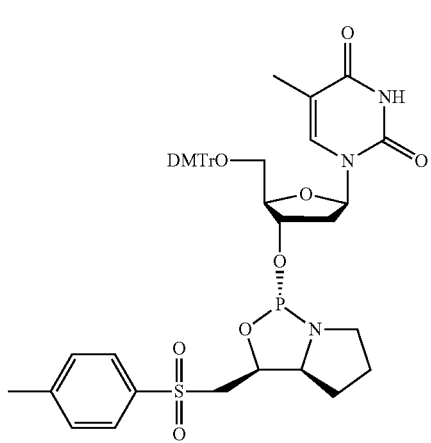

Compound 24a was obtained by using XIII-a instead of III-a in a similar manner to compound 4a.

¹H NMR (600 MHz, CDCl₃) d 7.76 (2H, d, J=9.0 Hz), 7.62 (1H, d, J=1.2 Hz), 7.40 (2H, d, J=7.2 Hz), 7.32-7.23

(10H, m), 6.85 (4H, d, J=8.4 Hz), 6.41 (1H, dd, J=8.4, 5.4 Hz), 4.94 (1H, dd, J=12.3, 5.4 Hz), 4.84-4.79 (1H, m), 4.03-4.01 (1H, m), 3.79 (6H, s), 3.59-3.53 (1H, m), 3.52-3.44 (2H, m), 3.41 (1H, dd, J=14.7, 7.2 Hz), 3.37-3.30 (2H, m), 3.13 (1H, ddd, J=19.3, 10.3, 4.1 Hz), 2.50-2.44 (1H, m), 2.39 (3H, s), 2.35-2.29 (1H, m), 1.91-1.72 (2H, m), 1.64-1.59 (1H, m), 1.40 (3H, s), 1.12-1.05 (1H, in); $^{31}$P NMR (243.0 MHz, CDCl$_3$) d 154.2 (1P, s).

General Procedure for the Synthesis of Chiral-Oligos:

The automated solid-phase synthesis of chiral-oligos were performed according to the cycles shown in Table 1. After the synthesis, the resin was treated with a 25% NH$_3$ aqueous solution (1 mL) for 12 h at 55 degrees C. The mixture was cooled to room temperature and the resin was removed by membrane filtration. The filtrate was concentrated to dryness under reduced pressure. The residue was dissolved in H$_2$O (3 mL) and analyzed by RP-UPLC-MS with a linear gradient of acetonitrile (0-50%/30 min) in 0.1 M triethylammonium acetate buffer (pH 7.0) at 50 degrees C. at a rate of 0.3 mL/min.

TABLE 1

| step | operation | reagents and solvent | volume | waiting |
|---|---|---|---|---|
| 1 | detritylation | 3% DCA/DCM | 1.6 mL | 20 s |
| 2 | coupling | 0.1M monomer/MeCN + 1M | 0.5 mL | 5 min |
| 3 | capping | Ac$_2$O/THF-pyridine + 16%/THF | 0.5 mL | 30 s |
| 4 | oxidation/ urization | 0.5M CSO/MeCN or 0.1M MeCN | 0.5 mL | 90 s |

Comparison Example 1

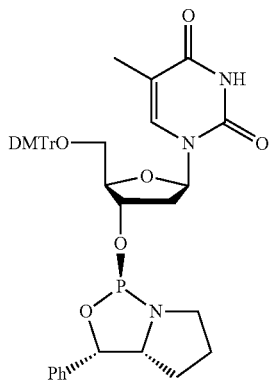

Figure 2:
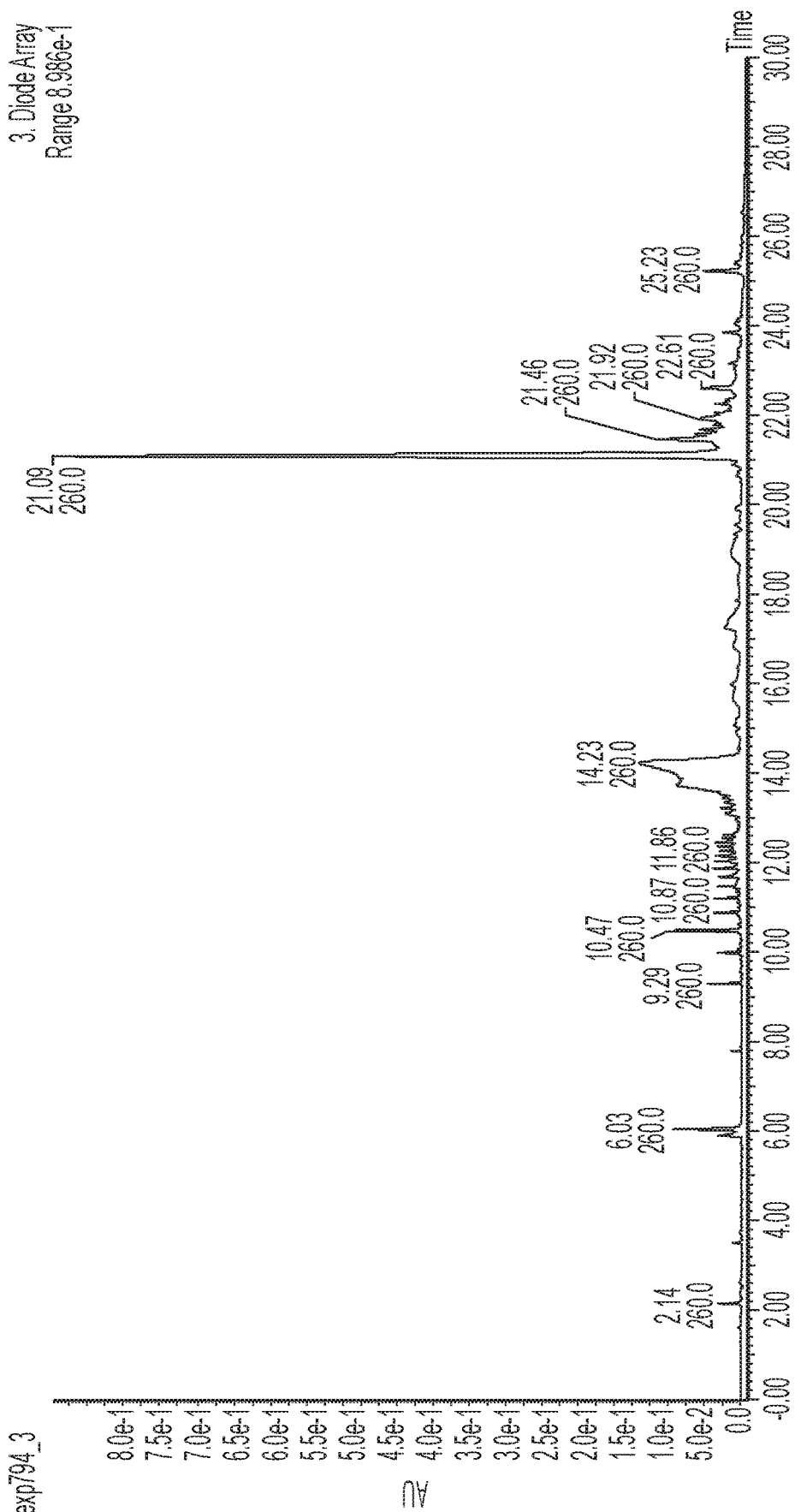
FIG. 2 is UPLC profile in producing oligonucleotide derivative using the monomer of 25.

The above Compound 25, which represents a conventional monomer, was used to produce oligos. FIG. 2 shows a chart of products obtained through Comparison Example 1.

Analysis

The monomers of the working examples were chemically stable. The isolate yield of the monomers were more than 80%, which was higher that of conventional method.

We synthesized oligonucleotide derivatives using the chiral reagents of the above working examples based on the second general procedure and monomers of the above working examples based on the first general procedure. As shown in FIG. 2, the conventional monomer causes incomplete de-protection products, side products and failure sequences. On the other hand, the method of the invention causes little incomplete de-protection products and little side products even though it causes failure sequences as shown in FIG. 1. It is obvious that the method of the invention can lessen the incomplete de-protection products and side products. It was easy to isolate the targeted oligonucleotide derivatives because the present invention can lessen undesirable products.

The invention claimed is:

1. An oligonucleotide on a solid support having the structure of:

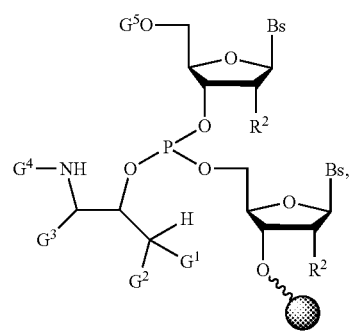

wherein:

$G^1$ is a hydrogen atom, a nitro group, a halogen atom, a cyano group, or a group of formula (II), (III) or (V);

$G^2$ is a nitro group, a halogen atom, a cyano group, or a group of formula (II), (III), or (V); or both $G^1$ and $G^2$ are taken together to form a group of formula (IV);

wherein formula (II) is:

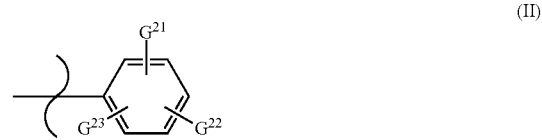

and $G^{21}$ to $G^{23}$ are independently a hydrogen atom, a nitro group, a halogen atom, a cyano group or $C_{1-3}$ alkyl group;

wherein formula (III) is:

and $G^{31}$ to $G^{33}$ are independently $C_{1-4}$ alkyl group, $C_{1-4}$ alkoxy group, $C_{6-14}$ aryl group, $C_{7-14}$ aralkyl group, $C_{1-4}$ alkyl $C_{6-14}$ aryl group, $C_{1-4}$ alkoxy $C_{6-14}$ aryl group, or $C_{6-14}$ aryl $C_{1-4}$ alkyl group;

wherein formula (IV) is:

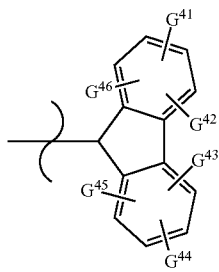
(IV)

and
G$^{41}$ to G$^{46}$ are independently a hydrogen atom, a nitro group, a halogen atom, a cyano group or C$_{1-3}$ alkyl group;
wherein formula (V) is:

(V)

and
G$^{51}$ to G$^{53}$ are independently a hydrogen atom, a nitro group, a halogen atom, a cyano group, C$_{1-3}$ alkyl group or C$_{1-3}$ alkyloxy group,
G$^3$ and G$^4$ are independently a hydrogen atom, C$_{1-3}$ alkyl group, C$_{6-14}$ aryl group, or both G$^3$ and G$^4$ are taken together to form a heteroatom-containing ring that has 3 to 16 carbon atoms;
G$^5$ is a protective group of a hydroxyl group;
each R$^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^b$, wherein R$^b$ is a blocking moiety;
Y$^1$ is O, NR$^d$, S, or Se;
R$^d$ is independently hydrogen, alkyl, alkenyl, alkynyl, aryl, acyl, substituted silyl, carbamate, —P(O)(R$^e$)$_2$, or —HP(O)(R$^e$);
R$^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^+$, Li$^+$, or K$^+$;
Y$^2$ is O, S, or NR$^d$ wherein R$^d$ is independently hydrogen, alkyl, alkenyl, alkynyl, aryl, acyl, substituted silyl, or carbamate;

represents a solid support optionally with a linking moiety; and
each Bs is independently a group selected from the groups represented by following formula (VI) to (XI) or derivatives thereof:

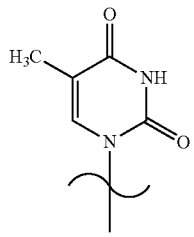
(VI)

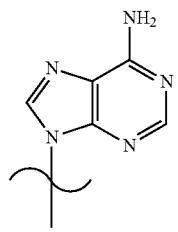
(VII)

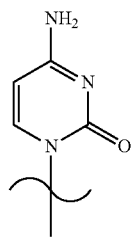
(VIII)

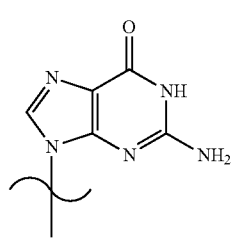
(IX)

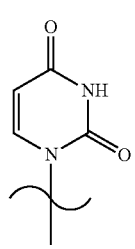
(X)

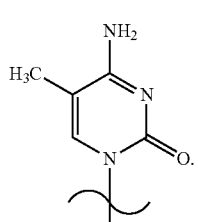
(XI)

2. The oligonucleotide of claim 1, wherein G$^3$ and G$^4$ are taken together to form a heteroatom-containing ring that has 3 to 16 carbon atoms.

3. The oligonucleotide of claim 1, wherein G$^3$ and G$^4$ are taken together to form a heteroatom-containing ring that has 4 carbon atoms.

4. The oligonucleotide of claim 1, wherein $G^1$ is a hydrogen atom, a nitro group, a halogen atom, a cyano group, or a group of formula (II), (III) or (V).

5. The oligonucleotide of claim 1, wherein $G^2$ is a nitro group, a cyano group, or a group of formula (II), (III) or (V), or both $G^1$ and $G^2$ are taken together to form a group of formula (IV).

6. The oligonucleotide of claim 1, wherein $G^1$ is a hydrogen atom.

7. The oligonucleotide of claim 1, wherein each of $G^1$ and $G^2$ is a group of formula (II), wherein $G^{21}$ to $G^{23}$ are independently a hydrogen atom, a nitro group, a halogen atom, a cyano group, or $C_{1-3}$ alkyl group.

8. The oligonucleotide of claim 1, wherein each of $G^1$ and $G^2$ is a group of formula (II), wherein each of $G^{21}$ to $G^{23}$ is a hydrogen atom.

9. The oligonucleotide of claim 1, wherein $G^2$ is a group of formula (II), wherein $G^{21}$ to $G^{23}$ are independently a hydrogen atom, a nitro group, a halogen atom, a cyano group or $C_{1-3}$ alkyl group.

10. The oligonucleotide of claim 1, wherein $G^2$ is a group of formula (II), wherein each of $G^{21}$ and $G^{22}$ is a hydrogen atom and $G^{23}$ is a nitro group.

11. The oligonucleotide of claim 1, wherein $G^2$ is a group of formula (III), wherein $G^{31}$ to $G^{33}$ are independently $C_{1-4}$ alkyl group, $C_{6-14}$ aryl group, $C_{7-14}$ aralkyl group, $C_{1-4}$ alkyl $C_{6-14}$ aryl group, $C_{1-4}$ alkoxy $C_{6-14}$ aryl group, or $C_{6-14}$ aryl $C_{1-4}$ alkyl group.

12. The oligonucleotide of claim 1, wherein $G^2$ is a group of formula (III), wherein $G^{31}$ to $G^{33}$ are independently $C_{1-4}$ alkyl group, $C_6$ aryl group, $C_{7-10}$ aralkyl group, $C_{1-4}$ alkyl $C_6$ aryl group, $C_{1-4}$ alkoxy $C_6$ aryl group, or $C_6$ aryl $C_{1-4}$ alkyl group.

13. The oligonucleotide of claim 1, wherein $G^2$ is a group of formula (III), wherein $G^{31}$ to $G^{33}$ are independently $C_{1-4}$ alkyl group, or $C_6$ aryl group.

14. The oligonucleotide of claim 1, wherein $G^2$ is a group of formula (III), wherein $G^{31}$ to $G^{33}$ are independently $C_{1-4}$ alkyl group.

15. The oligonucleotide of claim 1, wherein $G^2$ is a group of formula (III), wherein $G^{31}$ and $G^{33}$ are $C_6$ aryl group and $G^{32}$ is $C_{1-4}$ alkyl group.

16. The oligonucleotide of claim 1, wherein $G^2$ is a group of formula (III), wherein the $C_{1-4}$ alkyl group is a methyl group.

17. The oligonucleotide of claim 1, wherein $G^2$ is a group of formula (III), wherein $G^{31}$ and $G^{33}$ are phenyl.

18. The oligonucleotide of claim 1, wherein $G^1$ and $G^2$ are taken together to form a group of formula (IV), wherein $G^{41}$ to $G^{46}$ are independently a hydrogen atom, a nitro group, a halogen atom, a cyano group, or $C_{1-3}$ alkyl group.

19. The oligonucleotide of claim 1, wherein $G^1$ and $G^2$ are taken together to form a group of formula (IV), wherein each of $G^{41}$ to $G^{46}$ is a hydrogen atom.

20. The oligonucleotide of claim 1, wherein $G^2$ is a group of formula (V), wherein each of $G^{51}$ to $G^{53}$ are independently a hydrogen atom, a nitro group, a methyl group, or a methoxy group.

21. The oligonucleotide of claim 1, wherein $G^2$ is a group of formula (V), wherein each of $G^{51}$ and $G^{53}$ is a hydrogen atom and $G^{53}$ is a 4-methyl group.

22. The oligonucleotide of claim 1, wherein a $R^2$ is hydrogen.

23. The oligonucleotide of claim 1, wherein a $R^2$ is halogen.

24. The oligonucleotide of claim 1, wherein a $R^2$ is alkyl-$Y^1$—, alkenyl-$Y^1$—, alkynyl-$Y^1$—, aryl-$Y^1$—, or heteroaryl-$Y^1$—.

25. The oligonucleotide of claim 1, wherein a $R^2$ is alkyl-$Y^1$—.

26. The oligonucleotide of claim 1, wherein $Y^1$ is O.

27. The oligonucleotide of claim 1, wherein $G^5$ is trityl, 4-monomethoxytrityl, 4,4'-dimethoxytrityl, 4,4',4''-trimethoxytrityl, 9-phenylxanthin-9-yl (Pixyl) or 9-(p-methoxyphenyl)xanthin-9-yl (MOX).

28. The oligonucleotide of claim 1, wherein $G^5$ is 4,4'-dimethoxytrityl.

29. The oligonucleotide of claim 1, wherein Bs is independently an adenine, a thymine, a cytosine, a guanine, or a derivative thereof.

30. The oligonucleotide of claim 1, wherein each Bs is independently selected from:

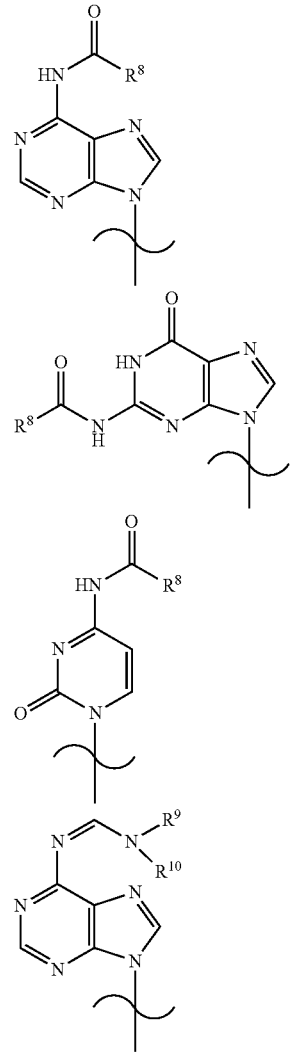

-continued
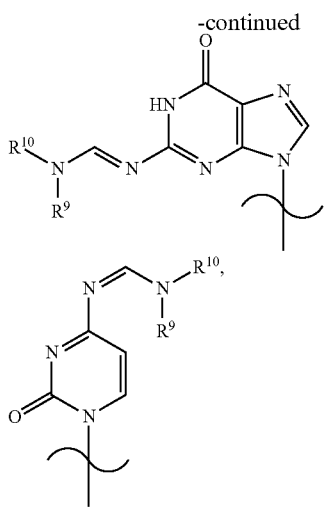
wherein each of $R^8$ to $R^{10}$ is independently $C_{1-10}$ alkyl, $C_6$-$C_{10}$ aryl, $C_6$-$C_{10}$ aralkyl, or $C_6$-$C_{10}$ aryloxyalkyl.
31. The oligonucleotide of claim 30, wherein $R^8$ is methyl, isopropyl, phenyl, benzyl, or phenoxymethyl.
32. The oligonucleotide of claim 30, wherein $R^9$ and $R^{10}$ are $C_{1-4}$ alkyl group.
* * * * *